United States Patent
Brehm et al.

(10) Patent No.: US 10,062,168 B2
(45) Date of Patent: Aug. 28, 2018

(54) 5D CONE BEAM CT USING DEFORMABLE REGISTRATION

(71) Applicant: Varian Medical Systems International AG, Cham (CH)

(72) Inventors: Marcus Brehm, Zurich (CH); Marc Kachelriess, Nuremberg (DE); Pascal Paysan, Basel (CH)

(73) Assignee: Varian Medical Systems International AG, Chan (CH)

( * ) Notice: Subject to any disclaimer, the term of this patent is extended or adjusted under 35 U.S.C. 154(b) by 110 days.

(21) Appl. No.: 15/055,495

(22) Filed: Feb. 26, 2016

(65) Prior Publication Data
US 2017/0249740 A1 Aug. 31, 2017

(51) Int. Cl.
G06K 9/00 (2006.01)
G06T 7/00 (2017.01)
G06T 15/08 (2011.01)
A61B 6/03 (2006.01)
A61B 6/00 (2006.01)

(52) U.S. Cl.
CPC ............ *G06T 7/0026* (2013.01); *A61B 6/032* (2013.01); *A61B 6/486* (2013.01); *A61B 6/5235* (2013.01); *G06T 15/08* (2013.01); *G06T 2207/10081* (2013.01); *G06T 2207/30048* (2013.01)

(58) Field of Classification Search
CPC .................. G06T 7/0026; G06T 15/08; G06T 2207/10081; G06T 2207/30048; A61B 6/032; A61B 6/486; A61B 6/5235
See application file for complete search history.

(56) References Cited

U.S. PATENT DOCUMENTS

| 6,865,248 | B1 | 3/2005 | Rasche et al. |
| 9,047,701 | B2 | 6/2015 | Brehm et al. |
| 9,245,336 | B2 * | 1/2016 | Mallya ...................... G06T 7/30 |
| 2007/0025509 | A1 | 2/2007 | Pang et al. |

(Continued)

FOREIGN PATENT DOCUMENTS

| WO | WO 2006/003002 | 1/2006 |
| WO | WO 2006/119623 | 11/2006 |

OTHER PUBLICATIONS

Li, Tianfang, Albert Koong, and Lei Xing. "Enhanced 4D cone-beam CT with inter-phase motion model." Medical physics 34.9 (2007): 3688-3695.*

(Continued)

*Primary Examiner* — Shefali Goradia
(74) *Attorney, Agent, or Firm* — Vista IP Law Group, LLP

(57) ABSTRACT

An apparatus includes: an input configured to receive a plurality of images, wherein the images include respective sub-images of a bodily part of a subject, and wherein a position of the bodily part relates to a breathing movement and a cardiac movement of the subject; a first registration engine configured to determine a first registration of at least two breathing correlated images, wherein the at least two breathing correlated images comprise two of the plurality of images or are derived from at least some of the plurality of images; a second registration engine configured to determine a second registration of at least two cardiac correlated images; and a volumetric image generator configured to generate a volumetric image using the first registration and the second registration.

29 Claims, 20 Drawing Sheets

(56) References Cited

U.S. PATENT DOCUMENTS

| | | | |
|---|---|---|---|
| 2007/0189591 A1 | 8/2007 | Lu et al. | |
| 2008/0177280 A1* | 7/2008 | Adler | A61N 5/1049 606/130 |
| 2010/0172567 A1* | 7/2010 | Prokoski | A61B 5/0064 382/132 |
| 2010/0201786 A1 | 8/2010 | Schaefer et al. | |
| 2011/0176723 A1 | 7/2011 | Ali et al. | |
| 2011/0206178 A1 | 8/2011 | Van Herk et al. | |
| 2011/0299751 A1 | 12/2011 | Nord et al. | |
| 2011/0311118 A1 | 12/2011 | Shekhar et al. | |
| 2012/0245453 A1 | 9/2012 | Tryggestad et al. | |
| 2012/0281897 A1 | 11/2012 | Razifar et al. | |
| 2013/0223702 A1* | 8/2013 | Holsing | A61B 5/113 382/128 |
| 2013/0259338 A1* | 10/2013 | Brehm | A61B 6/5235 382/131 |
| 2017/0189721 A1* | 7/2017 | Sumanaweera | A61N 5/1067 |

OTHER PUBLICATIONS

Li et al., "Advances in 4D medical imaging and 4D radiation therapy", Technol. Cancer Res. Treat., 7 (1) (2008), pp. 67-81.*

Brehm, Marcus, et al., "Cardiorespiratory motion-compensated micro-CT image reconstruction using an artifact model-based motion estimation," Medical Physics 42, 2015 (12 pages).

Brehm, Marcus, et al., "Robust Motion Estimation for On-Board CBCT Imaging using an Angular Sampling Artifact Model," dated Jun. 5, 2013 (4 pages).

Brehm, Marcus, et al., "Artifact-Resistant motion estimation with a patient-specific artifact model for motion-compensated cone-beam CT," Med. Phys. 40, 101913, 2013.

Brehm, Marcus, et al., "Artefakt-resistente Bewegungsschatzung fur die bewegungskompensierte CT" in Abstractband zur 44. Jahrestagung der Deutschen Gesellschaft fur Medizinische Physik, 232-234, 2013.

Brehm, Marcus, et al., "Artifact-Resistant motion estimation for motion-compensated CT," in Program of the 99$^{th}$ Scientific Assembly and Annual Meeting of the RSNA, 2013.

T. Li et al., "Four-dimensional cone-beam computed tomography using an on-board imager" Med. Phys., vol. 33, No. 10, 9 pages, Oct. 2006.

S. Leng et al., "Streaking artifacts reduction in four-dimensional cone-beam computed tomography" Med. Phys., vol. 35, No. 10, 11 pages, Oct. 2008.

J.-P. Thirion, "Image matching as a diffusion process: An analogy with Maxwell's demons", Medical Image Analysis, vol. 2, No. 3, 18 pages, Sep. 1998.

H. Wang et al., "Validation of an accelerated 'demons' algorithm for deformable image registration in radiation therapy", Phys. Med. Biol., vol. 50, No. 12, 20 pages, Jun. 2005.

J. Lu et al., "Four-dimensional cone beam CT with adaptive gantry rotation and adaptive data sampling", Med. Phys., vol. 34, No. 9, 10 pages, Sep. 2007.

T. Li et al., "Motion correction for improved target localization with on-board cone-beam computed tomography" Phys. Med. Biol., vol. 51, No. 2, 2 pages, Feb. 2006.

S. Rit et al., "On-the-fly motion-compensated cone-beam CT using an a priori model of the respiratory motion" Med. Phys. vol. 36, No. 6, 8 pages, Jun. 2009.

International Search Report and Written Opinion dated Jul. 8, 2013 for PCT Application No. PCT/US2013/034706, 9 pages.

* cited by examiner

5D CONE BEAM CT USING DEFORMABLE REGISTRATION

FIELD

This application relates to systems and methods for obtaining one or more volumetric images.

BACKGROUND

Sometimes, for diagnostic purposes and/or for radiation treatment planning, the target region of the patient may be imaged using a CT system. For example, CT imaging may have interventional and surgical applications, e.g., checking if inserted heart valve is working properly. As another example, cone beam CT (CBCT) imaging may be performed to check patient positioning, setup patient, etc. For the case in which the target region moves in a periodic motion (e.g., due to breathing and/or cardiac motion), the CT system may be used to determine volumetric images of the target when the target is at different breathing states and/or cardiac states, so that the volumetric images may be played back as respective video streams for breathing motion and cardiac motion. To this end, projection images of a target patient at various breathing and cardiac states are obtained.

After the imaging session, the projection images at various stages of a breathing or cardiac cycle are sorted into different sets according to the recorded states of the patient when the corresponding projection images are acquired. For example, the projection images may be sorted according to the phase of the physiological cycle at which they are generated, so that projection images are sorted into different phase bins. After the projection images are sorted, the projection images in each of the phase bin are then used to reconstruct a volumetric image for that phase bins. Alternatively, projection images may be sorted according to the breathing amplitudes of the physiological cycle, so that the projection images are sorted into different amplitude bins. As used in this specification, the term "bin" may refer to phase bin or amplitude bin. Further details on reconstructing volumetric images based on breathing states are disclosed in U.S. patent application Ser. No. 13/436,908, now issued as U.S. Pat. No. 9,047,701, which is herein incorporated by reference in its entirety for all purposes.

However, when taking both breathing motion and cardiac motion in account, improved approaches are required to appropriately sort the various images into respective combined phase bins that correspond to both breathing motion and cardiac motion, and to accurately reconstruct volumetric images for these combined phase bins.

BRIEF DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments and are not therefore to be considered limiting of its scope.

SUMMARY

Figure 1:
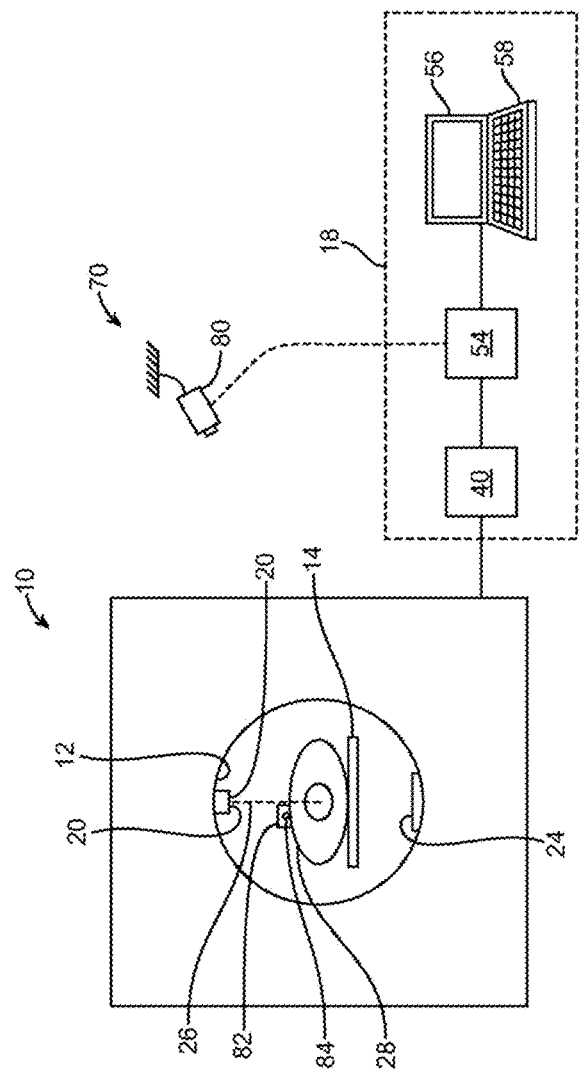
FIG. 1 illustrates a radiation system in accordance with some embodiments.

An apparatus includes: an input configured to receive a plurality of images, wherein the images include respective sub-images of a bodily part of a subject, and wherein a position of the bodily part relates to a breathing movement and a cardiac movement of the subject; a first registration engine configured to determine a first registration of at least two breathing correlated images, wherein the at least two breathing correlated images comprise two of the plurality of images or are derived from at least some of the plurality of images; a second registration engine configured to determine a second registration of at least two cardiac correlated images; and a volumetric image generator configured to generate a volumetric image using the first registration and the second registration.

Optionally, the first registration comprises a 2D-to-2D image registration.

Optionally, the first registration comprises a 3D-to-3D image registration.

Optionally, the first registration comprises a 2D-to-3D image registration.

Optionally, the at least two breathing correlated images are generated during an imaging session.

Optionally, the at least two breathing correlated images correspond with different respective breathing bins, and wherein each of the at least two breathing correlated images comprises image data that are for a same one of the breathing bins.

Optionally, the at least two cardiac correlated images correspond with different respective cardiac bins, and wherein each of the at least two cardiac correlated images comprises image data that are for a same one of the cardiac bins.

Optionally, the apparatus further includes a cardiac correlated image generator configured to generate the at least two cardiac correlated images.

Optionally, the cardiac correlated image generator is configured to generate the at least two cardiac correlated images based on the first registration.

Optionally, the apparatus further includes a non-transitory medium storing the plurality of images in association with a number N1 of breathing stages and in association with a number N2 of cardiac stages.

Optionally, the apparatus further includes a breathing-cardiac image generator configured to generate N1×N2 number of breathing-cardiac images for the different combinations of breathing-cardiac stages.

Optionally, the cardiac correlated image generator is configured to generate the at least two cardiac correlated images based on the first registration and based on a subset of the N1×N2 number of breathing-cardiac images.

Optionally, the volumetric image generator is configured to generate the volumetric image also using at least 50% of the plurality of images, wherein the plurality of images is generated while the subject is undergoing different breathing stages and cardiac stages.

Optionally, the volumetric image generator is configured to generate the volumetric image also using at all of the plurality of images, wherein the plurality of images is generated while the subject is undergoing different breathing stages and cardiac stages.

Optionally, the first registration comprises a deformation registration.

Optionally, the second registration comprises a deformation registration.

An image processing method includes: obtaining a plurality of images, wherein the images include respective sub-images of a bodily part of a subject, and wherein a position of the bodily part relates to a breathing movement and a cardiac movement of the subject; determining, using a first registration engine, a first registration of at least two breathing correlated images, wherein the at least two breathing correlated images comprise two of the plurality of images or are derived from at least some of the plurality of images; determining, using a second registration engine, a second registration of at least two cardiac correlated images; and generating, using a volumetric image generator, a volumetric image using the first registration and the second registration.

Optionally, the first registration comprises a 2D-to-2D image registration.

Optionally, the first registration comprises a 3D-to-3D image registration.

Optionally, the first registration comprises a 2D-to-3D image registration.

Optionally, the at least two breathing correlated images are generated during an imaging session.

Optionally, the at least two breathing correlated images correspond with different respective breathing bins, and wherein each of the at least two breathing correlated images comprises image data that are for a same one of the breathing bins.

Optionally, the at least two cardiac correlated images correspond with different respective cardiac bins, and wherein each of the at least two cardiac correlated images comprises image data that are for a same one of the cardiac bins.

Optionally, the method further includes generating, using a cardiac correlated image generator, the at least two cardiac correlated images.

Optionally, the at least two cardiac correlated images are generated based on the first registration.

Optionally, the method further includes storing the plurality of images in association with a number N1 of breathing stages and in association with a number N2 of cardiac stages.

Optionally, the method further includes generating, using a breathing-cardiac image generator, N1×N2 number of breathing-cardiac images for the different combinations of breathing-cardiac stages.

Optionally, the at least two cardiac correlated images are generated based on the first registration and based on a subset of the N1×N2 number of breathing-cardiac images.

Optionally, the volumetric image is generated also using at least 50% of the plurality of images, wherein the plurality of images is generated while the subject is undergoing different breathing stages and cardiac stages.

Optionally, the volumetric image is generated also using at all of the plurality of images, wherein the plurality of images is generated while the subject is undergoing different breathing stages and cardiac stages.

A product includes a non-transitory medium storing a set of instruction, an execution of which causes a process to be performed, the process comprising: obtaining a plurality of images, wherein the images include respective sub-images of a bodily part of a subject, and wherein a position of the bodily part relates to a breathing movement and a cardiac movement of the subject; determining, using a first registration engine, a first registration of at least two breathing correlated images, wherein the at least two breathing correlated images comprise two of the plurality of images or are derived from at least some of the plurality of images; determining, using a second registration engine, a second registration of at least two cardiac correlated images; and generating, using a volumetric image generator, a volumetric image using the first registration and the second registration.

Optionally, the first registration comprises a deformation registration.

Optionally, the second registration comprises a deformation registration.

Other features, advantageous, and embodiments will be described in the detailed description.

DESCRIPTION OF THE EMBODIMENTS

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment need not have all the aspects or advantages shown. An aspect or an advantage described in conjunction with a particular embodiment is not necessarily limited to that embodiment and can be practiced in any other embodiments even if not so illustrated.

FIG. 1 illustrates an imaging system 10 in accordance with some embodiments. The system 10 includes a gantry 12, and a panel 14 for supporting a patient 28. The gantry 12 includes a radiation source 20 that projects a beam 26 of radiation (e.g., x-rays) towards a detector 24 on an opposite side of the gantry 12 while the patient 28 is positioned at least partially between the radiation source 20 and the detector (imager) 24. By means of non-limiting examples, the beam of x-rays can be a cone beam or a fan beam. The detector 24 has a plurality of sensor elements configured for sensing an x-ray that passes through the patient 28. Each sensor element generates an electrical signal representative of an intensity of the x-ray beam as it passes through the patient 28. The system 10 also includes a positioner (not shown) configured to move the radiation source 20. In some embodiments, the positioner may be configured to rotate the gantry 12 to thereby turn the radiation source 20 along a circular or an arc path.

The system 10 also includes a control system 18. In the illustrated embodiments, the control system 18 includes a processor 54, such as a computer processor, coupled to a control 40. The control system 18 may also include a monitor 56 for displaying data and an input device 58, such as a keyboard or a mouse, for inputting data. The operation of the radiation source 20 and the gantry 12 are controlled by the control 40, which provides power and timing signals to the radiation source 20, and controls a rotational speed and position of the gantry 12, based on signals received from the processor 54. Although the control 40 is shown as a separate component from the gantry 12 and the processor 54, in alternative embodiments, the control 40 can be a part of the gantry 12 or the processor 54.

In the illustrated embodiments, the radiation source 20 is a diagnostic radiation source for providing diagnostic energy. In other embodiments, in addition to, or instead of, being a diagnostic radiation source, the radiation source 20 may be a treatment radiation source for providing treatment energy. In some embodiments, the treatment energy is generally those energies of 160 kilo-electron-volts (keV) or greater, and more typically 1 mega-electron-volts (MeV) or greater, and diagnostic energy is generally those energies below the high energy range, and more typically below 160 keV. In other embodiments, the treatment energy and the diagnostic energy can have other energy levels, and refer to energies that are used for treatment and diagnostic purposes, respectively. In some embodiments, the radiation source 20 is able to generate X-ray radiation at a plurality of photon energy levels within a range anywhere between approximately 10 keV and approximately 20 MeV. In further embodiments, the radiation source 20 may be a treatment radiation source, in which cases, the imager 24 may be an on-board imager.

In still further embodiments, the radiation source 20 may be an additional source that is not used for treatment or diagnostic purposes.

It should be noted that the system 10 is not limited to the configuration described above, and that the system 10 may have other configurations in other embodiments. For example, in other embodiments, the system 10 may have a different shape. In other embodiments, the radiation source 20 of the system 10 may have different ranges of motions and/or degrees of freedom. For example, in other embodiments, the radiation source 20 may be rotatable about the patient 28 completely through a 360° range, or partially through a range that is less than 360°. Also, in other embodiments, the radiation source 20 is translatable relative to the patient 28. In some embodiments, the system 10 may be a CT system. In other embodiments, the system 10 may be a radiation treatment system. In such cases, the radiation source 20 is not limited to delivering diagnostic energy in the form of x-ray, and may deliver treatment energy for treating a patient. Also, in some embodiments, the gantry 12 of the system 10 may cooperate with the patient support 14 to achieve a spiral motion. For example, the gantry 12 may rotate while the patient support 14 is being translated along its longitudinal axis.

During a scan to acquire x-ray image data (projection data), the gantry 12 rotates about the patient 28 at different gantry angles, so that the radiation source 20 and the imager 24 may be used to obtain images at different gantry angles. As the system 10 is operated to obtain images at different gantry angles, the patient 28 is experiencing movement related to various physiological cycles, like breathing motion or cardiac motion. Thus, the resulting images at different gantry angles may correspond to different phases of the physiological cycle (e.g., breathing cycle, cardiac cycle, etc.) for the patient 28. After the scan is completed, or while the scan is continued to obtain additional projection images, the generated projection images at different gantry angles are stored, e.g., in a memory, and the projection images are processed to sort the images so that images that correspond to a same phase or a same phase range of a physiological cycle are binned (e.g., associated with each other). The binned images for a specific phase of a physiological cycle can then be used to reconstruct a digital volumetric image for that phase.

As shown in the figure, the system 10 may optionally further include a patient position determining system 70 that includes a camera 80 and a marker block 82 having a plurality of markers 84. The patient position determining system 70 is configured to determine amplitude and/or phase of a physiological movement of the patient 28. During use, the marker block 82 may be placed on the patient's chest, and the camera 80 is then used to view the markers 84 on the marker block 82. For example, during a respiratory cycle, the chest of the patient 28 will move up and down, and the marker block 82 will move correspondingly. Also, during a cardiac cycle, ECG may be performed for intrinsic gating to determine states of the patient relating to the cardiac cycle (e.g., cardiac phases, cardiac amplitudes, etc.). In other embodiments, marker approach may be used to determine cardiac phases/amplitudes.

Because the relative positions among the markers 84 on the block 82 are known and pre-determined, by using this information, the processor 54 may be configured to process the image(s) from the camera 80 to determine a position of the marker block 82 relative to some arbitrary reference coordinate. By continuously tracking the position of the marker block 82, the processor 54 may determine the amplitudes and/or phases of the physiological cycle that the patient 28 is going through. The determined amplitudes and/or phases may then be later used by the processor 54 to sort the images so that different sets of images correspond with respective phases or phase ranges of the physiological cycle (or combinations of ranges of different physiological cycles), as similarly discussed.

Alternatively, the camera 80 may be configured to use other things as marker(s), such as a patient's clothes, a physiological feature of the patient 28, etc. Thus, in other embodiments, the marker block 82 may be optional, and the patient position determining system 70 may not include any marker block 82. Examples of a patient position determining system include Varian's RPM product, which is capable of recording amplitudes and phases of a breathing signal along with image data. In other embodiments, the patient position determining system 70 may be other systems known in the art, such as a strain-gauge for measuring chest expansion, spirometer, etc., as long as the system can determine a state of the patient's 28 motion (e.g., breathing, cardiac motion, etc.). Also, in further embodiments, the patient position determining system 70 may use internal fiducial(s), such as implanted marker(s), anatomical feature(s), etc., for determining a state of a physiological cycle. In other embodiments, the patient position determining system 70 may use other techniques or components for determining states of a patient, such as spirometer, Doppler radar, intrinsic gating (e.g., using images taken from detector 24 for identifying internal fiducial(s)), etc.

Figure 2:
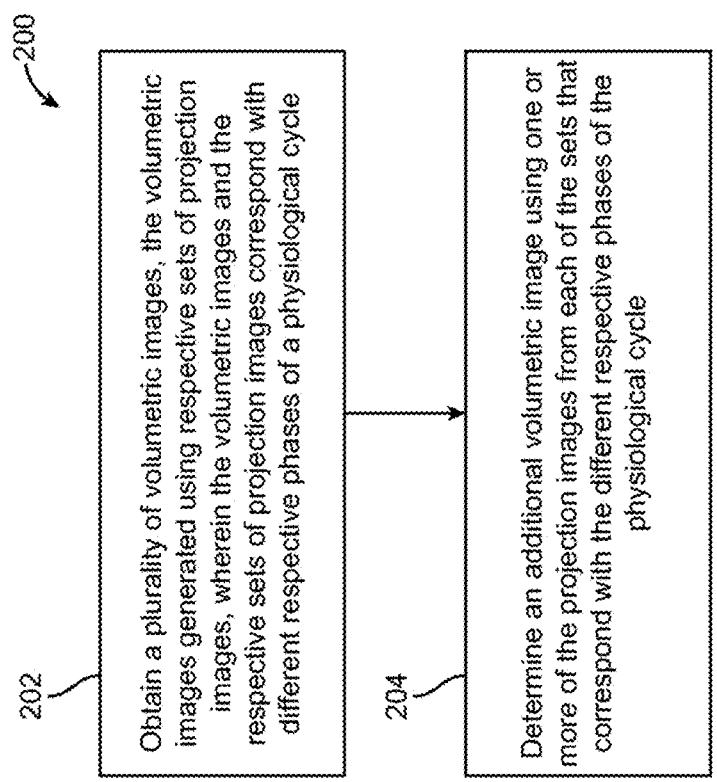
FIG. 2 illustrates a method of obtaining one or more volumetric images in accordance with some embodiments.

FIG. 2 illustrates a method 200 for determining a volumetric image in accordance with some embodiments. The method 200 will be described with reference to the system 10 of FIG. 1. However, it should be understood that the method 200 may be performed using other systems in other embodiments.

First, a plurality of volumetric images are obtained (Item 202). In the illustrated embodiments, the volumetric images are generated using respective sets of projection images (e.g., P1, P2, etc.), wherein the volumetric images and the respective sets of projection images correspond with different respective phases of a physiological cycle. For example, a first set of volumetric images may correspond to different phases of a breathing cycle. In one example embodiment, a sequence of these volumetric images may be used in order to create a video depicting movement of one or more body parts during various phases of a breathing cycle. Yet another set of volumetric images may correspond to different phases of a cardiac cycle. In another example embodiment, a sequence of this set of volumetric images may be used to create a video depicting movement of the one or more body parts during various phases of a cardiac cycle. Also, in other embodiments, there may be a set of volumetric images showing changes in both the breathing cycle and the cardiac cycle.

Figure 3:
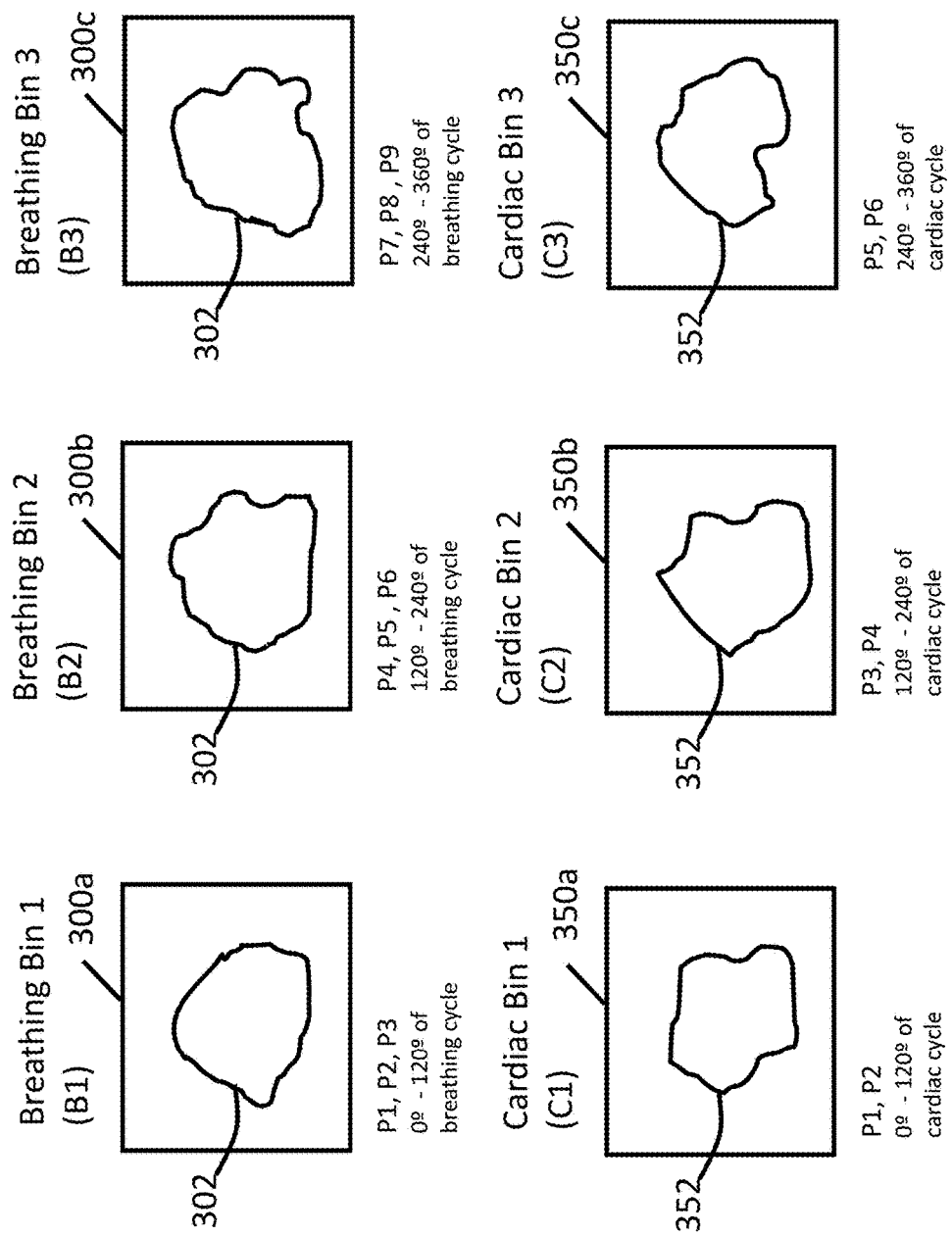
FIG. 3 illustrates different volumetric images for two physiological cycles obtained using the system of FIG. 1 in accordance with some embodiments.

FIG. 3 illustrates an example of two sequences of volumetric images (e.g., 300a-300c, and 350a-350c) which may be used to create respective videos depicting breathing motion and cardiac motion. In the illustrated embodiment, volumetric images 300a-300c depict a body part 302 while in different phases of the patient's breathing cycle. Similarly, volumetric images 350a-350c depict another (or same) body part 352 while in different phases of the patient's cardiac motion. It should be noted that the volumetric images 300a-300c for the breathing cycle, and the volumetric images 350a-350c for the cardiac cycle are shown separately for illustration of the concept described herein. In many cases, both motion patterns are not independent. In particular, cardiac position is affected by breathing motion. Thus, there may be a single set of volumetric images that show both the breathing motion and the cardiac motion.

Each volumetric image (e.g., 300 or 350) includes an image of the body part (e.g., 302 or 352). The volumetric images 300a-300c may be displayed in a sequence to form a video depicting the effect of breathing motion on the body part 302. Similarly, volumetric images 350a-350c may be displayed in a sequence to form a video depicting the effect of cardiac motion on the body part 352. Thus, these volumetric images allow a user to view how the body part moves in a physiological cycle (e.g., respiratory cycle, cardiac cycle, etc.). It should be appreciated that the above example utilizes a sequence of three volumetric images each for breathing and cardiac motion for illustrative purposes only, and other embodiments may utilize any number of volumetric images in a sequence to construct a video depicting the effect of the respective physiological cycle on the body part.

In the illustrated example, volumetric image 300a is generated using projection images P1, P2, P3 that correspond to phase 1 of the breathing cycle ("B1"), volumetric image 300b is generated using projection images P4, P5, P6 that correspond to phase 2 of the breathing cycle ("B2"), and volumetric image 300c is generated using projection images P7, P8, P9 that correspond to phase 3 of the breathing cycle ("B3"). Similarly, volumetric image 350a is generating using projection image P1, P2 that correspond to phase 1 of the cardiac cycle ("C1"), volumetric image 350b is generated using projection images P3, P4 that correspond to phase 2 of the cardiac cycle ("C2"), and volumetric image 350c is generated using projection images P5, P6 that correspond to phase 3 of the cardiac cycle ("C3"). Although two or three projection images are illustrated as being used to form a volumetric image, it should be understood that this is for illustrative purposes only, and that a volumetric image may be formed using more than three projection images.

The projection images P1-P9 may be generated using the system 10 (or another imaging system). While the projection images P1-P9 are being generated, there may be movement caused at least by the patient's breathing and the patient's cardiac motion. As a result, the projection images P1-P9 may correspond to different respective phases of breathing cycles and of cardiac cycles. In the illustrated embodiments, for each projection image that is obtained while the patient is at a certain phase of either the respiratory cycle or the cardiac cycle, the processor 54 receives signals from the patient position monitoring system that indicate the corresponding phase, and the processor 54 associates the image with the corresponding phase. The images and their respective associated phases may be stored in a non-transitory medium for later processing. After the projection images P1-P9 are generated, they may be sorted so that different projection images that are within a certain phase range are grouped. If there are more than one physiological cycles being tracked, projection images of a particular combination of phase ranges of the more than one physiological cycle may be grouped.

Since the breathing cycle and cardiac cycle of the patient is different (e.g., have different periods) in the illustrated embodiment, the projection images P1-P9 may be sorted differently based on the breathing cycle and cardiac cycle. For example, as shown in FIG. 3, projection image P3 belongs to phase 1 of the breathing cycle, but phase 2 of the cardiac cycle. In other words, projection image P3 is utilized to generate volumetric image 300a, and volumetric image 350b.

Further, it should be appreciated that projection images P7, P8 and P9 may be sorted based on the respective phase of the cardiac cycle, and used to generate the respective volumetric image, as will be described in further detail below. For example, projection images P7 and P8 may correspond to phase 1 of the cardiac cycle. Thus, P1, P2, P7 and P8 may be grouped together to generate volumetric image 350a.

In the illustrated example, projection images P1, P2, P3 are grouped into B1, projection images P4, P5, P6 are grouped into B2, projection images P7, P8, P9 are grouped into B3 in order to create respective volumetric images of the breathing cycle. Similarly, projection images P1, P2 are grouped into C1, projection images P3, P4 are grouped into C2, projection images P5, P6 are grouped into C3. As briefly discussed above, the remaining projection images P7, P8 and P9 may further be grouped into the three cardiac phases (e.g., P7, P8 may be grouped into C1, P9 may be grouped into C2, etc.), and used to generate respective volumetric images of the cardiac cycle.

In the illustrated embodiments, signals from the patient position monitoring system 70 may be used by the processor 54 to sort the projection images. In particular, while the imager 24 generates the projection images, the patient position monitoring system 70 is used to obtain position signals (e.g., in a form of camera images). The camera images are processed by the processor 54, which determines amplitudes of the respective physiological cycle. In other words, for every projection image captured, the processor 54 may determine a breathing amplitude, and a cardiac motion amplitude. The breathing amplitude may indicate what part of the breathing cycle the projection image was captured at, such that the projection image can be appropriately sorted into one of the respiratory phase bins (e.g., B1, B2 or B3). The cardiac motion amplitude may indicate what part of the cardiac cycle the projection image was captured at, such that the projection image can be sorted into one of the cardiac phase bins (e.g., C1, C2 or C3).

Figure 4:
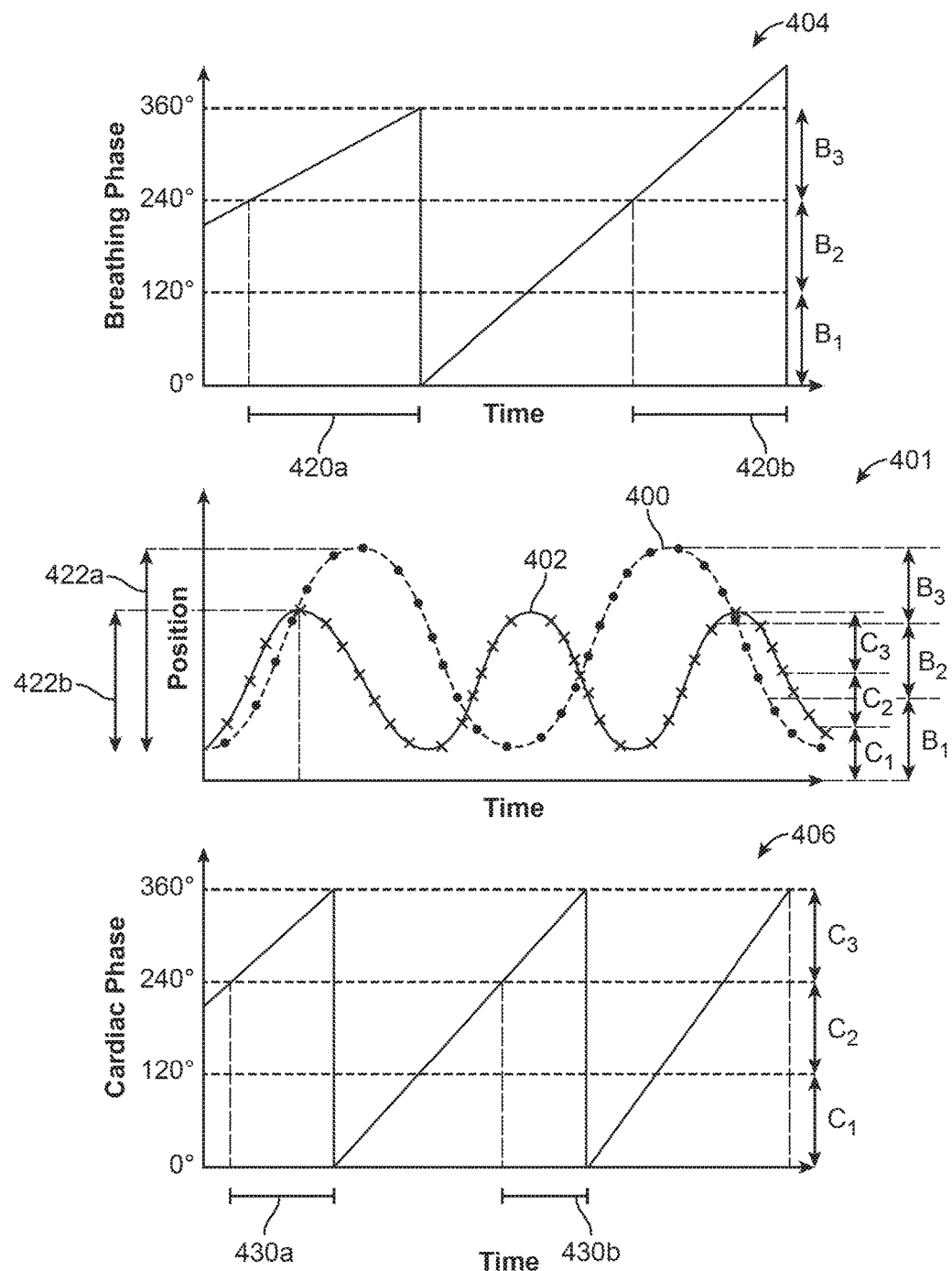
FIG. 4 illustrates phase diagrams for two physiological cycles aligned with corresponding amplitude diagrams in accordance with some embodiments.

FIG. 4 illustrates an example of the determined amplitudes of both respiratory and cardiac cycles plotted against time to form a breathing curve 400 and a cardiac curve 402 superimposed together in a single graph 401. In some embodiments, the processor 54 may also use the determined amplitudes to determine phases of the respective physiological cycle. A phase of the physiological cycle represents a degree of completeness of the physiological cycle. FIG. 4 also illustrates phase curves 404 and 406 having phase values plotted against time, wherein the phase curve 404 corresponds to the amplitude curve 400 pertaining to the breathing cycle, and the phase curve 406 corresponds to the amplitude curve 402 pertaining to the cardiac cycle. In the illustrated example, a phase value of 0° (and 360°) represents a peak of a physiological state, and the phase value varies linearly between 0° and 360° in a physiological cycle.

The examples of the phase bins (e.g., breathing phase bins B1-B3 and cardiac phase bins C1-C3) of both the respiratory cycle and the cardiac cycle are depicted in phase graphs 404 and 406 respectively. Breathing curve 400 depicts three phase bins B1, B2 and B3 for the respiratory cycle. B1 is for a phase range of, e.g., 0°-120°, B2 is for a phase range of, e.g., 120°-240°, and B3 is for a phase range of, e.g., 240°-360°. Similarly, cardiac curve 402 depicts three phase bins C1, C2 and C3 for the cardiac cycle. C1 is for a phase range of e.g., 0°-120°, C2 is for a phase range of, e.g., 120°-240°, and C3 is for a phase range of, e.g., 240°-360°. In such an example, the projection images will be grouped together based on the determined phase bins for the breathing cycle, and they will also be similarly grouped based on the determined phase bins for the cardiac cycle. In such an example, all projection images with breathing phase values from 0°-120°, 120°-240°, 240°-360° will be grouped by the processor 54 into breathing phase bins B1, B2 and B3 respectively. Similarly, all images with cardiac phase values 0°-120°, 120°-240°, 240°-360° will be grouped by the processor 54 into cardiac phase bins C1, C2 and C3 respectively.

For example, projection image P1 may be obtained when the patient is at breathing phase=45°, and projection image P2 may be obtained when the patient is at breathing phase=53°, and projection image P3 may be obtained when the patient is at breathing phase=80°. As a result, these three projection images P1, P2, P3 may be sorted by the processor 54 so that they are grouped into B1, which covers a breathing phase range of 0°-120°. The same projection image P1 may correspond to cardiac phase=70° and project image P2 may correspond to cardiac phase=110° so that they are grouped into C1 which covers a cardiac phase range of 0°-120°. However, P3 may correspond to cardiac phase=140°, and therefore may be binned into C2 instead. Similarly, the projection images P4, P5, P6 are generated when the patient is anywhere from 120°-240° in phase of a respiratory cycle, and thus, they are binned into B2. However, only projection images P3 and P4 may fall into 120°-240° in phase of the cardiac cycle, and thus, P3 and P4 may be binned into C2. Projection images P5 and P6 may fall into the 240° 360° of the cardiac phase range, and may be binned into C3. Finally, projection images P7, P8, P9 may be generated when the patient is anywhere from 240°-360° in phase of the respiratory cycle, and thus, they may be binned into B3. However, P7 and P8 may fall into the 0°-120° of the cardiac phase range, and may be binned into C1, whereas P9 may fall into the 120°-240° of the cardiac phase range and may be binned into C2. Thus, as discussed above, projection images may pertain to different phases of different physiological cycles, and may be binned accordingly.

The projection images P1, P2 and P3 may be generated during time durations 420a, 420b of the respiratory cycle, for example, as shown in phase graph 404 of FIG. 4. Similarly, projection images P1 and P2 may be generated during time durations 430a, 430b of the cardiac cycle, for example, as shown in phase graph 406 of FIG. 4. Note that the duration of the time periods 420a, 420b (or 430a, 430b) in the example are not necessarily equal, and that they may be different, depending on the breathing pattern (or cardiac movement pattern) of the patient 28.

It should be noted that the number of phase bins may not be limited to three, and that in other embodiments, the number of phase bins for sorting the projection images may be less than three, or more than three. Further, although the illustrated example comprises 3 respiratory phase bins and 3 cardiac phase bins, other embodiments may comprise different numbers of phase bins for different physiological cycles. Also, the number of phase bins of one physiological cycle may be different from the number of phase bins of another physiological cycle. For example, in another embodiment, there may be 2 cardiac phase bins, but 5 breathing phase bins.

Also, instead of having equal sizes, in some embodiments, the phase ranges in the respective bins may be different from each other. In addition, in some cases, a bin may cover two ranges that are next to each other (e.g., 0°-45° and 315°-360°), or two ranges that are separated from each other. In other embodiments, the phase ranges of the respective bins may overlap. For example, in some embodiments, phase bin 2 may be from 36° to 180°, phase bin 3 may be from 108° to 252°, phase bin 4 may be from 180° to 324°, etc. In such cases, the phase bins may provide double coverage. In other cases, the coverage may be smaller or greater than double (two times). In some embodiments, the number of bins may be user-prescribed. For example, a user may prescribe a certain number of phase bins (e.g., 3 phase bins) using the input device 58. Also, in some embodiments, the processor 54 may generate each volumetric image 300 or 302 using a subset of the projection images in each phase bin (set), so that not all of the projection images in each set are used for the construction of the volumetric image (e.g., 300, 350). In other embodiments, the processor 54 may use all of the projection images in each set to construct the volumetric image 300 or 350.

In some embodiments, the act of obtaining the volumetric images may be performed by a processor (e.g., processor 54) receiving the volumetric images. In other embodiments, the act of obtaining the volumetric images may be performed by a processor (e.g., processor 54), which receives projection images, sorts the projection images into different sets (bins) based on their respective phases, and reconstructs the volumetric images using the respective sets of sorted projection images. In some embodiments, the projection images and/or the volumetric images may be stored in a non-transitory medium for processing and/or retrieval later. Additionally, in some embodiments, the projection images and/or the volumetric images may be displayed in a screen (e.g., screen 56) for viewing by a user.

In the illustrated embodiments, the grouping of the projection images P is described as being based on the phase of the cycle. In other embodiments, the grouping of the projection images P may be based on amplitude of the cycle. For example, in some embodiments, the amplitude range 422a in a respiratory cycle 400 may be divided into a number of amplitude bins (e.g., three amplitude bins, as shown in the figure). Or, the amplitude range 422b in a cardiac cycle 402 may be divided into a number of amplitude bins (e.g., three amplitude bins as shown in the figure). In further embodiments, the grouping of the projection images P may be based on a combination of both techniques—e.g. one group of projection images P may be amplitude-based, and another group of the projection images P may be phase-based.

In such cases, projection images P that are generated when the amplitude is within the amplitude range of an amplitude bin are grouped into that bin. In other embodiments, the number of amplitude bins may be fewer than three, or more than three. Also, instead of having equal sizes, in some embodiments, the ranges (e.g., phase ranges, amplitude ranges, etc.) in the respective bins (e.g., phase bins, amplitude bins, etc.) may be different from each other. In further embodiments, the ranges in the respective bins (e.g., phase bins, amplitude bins, etc.) may overlap.

As discussed in detail above, the projection images (e.g., P1, P2, etc.) sorted in the various phase bins (e.g., B1, B2, etc., or C1, C2, etc.) are used to generate volumetric images 300 or 350 for each of the phase bins (e.g., $V_{B1}$, $V_{B2}$, $V_{C1}$, $V_{C2}$, etc.).

Figure 5:
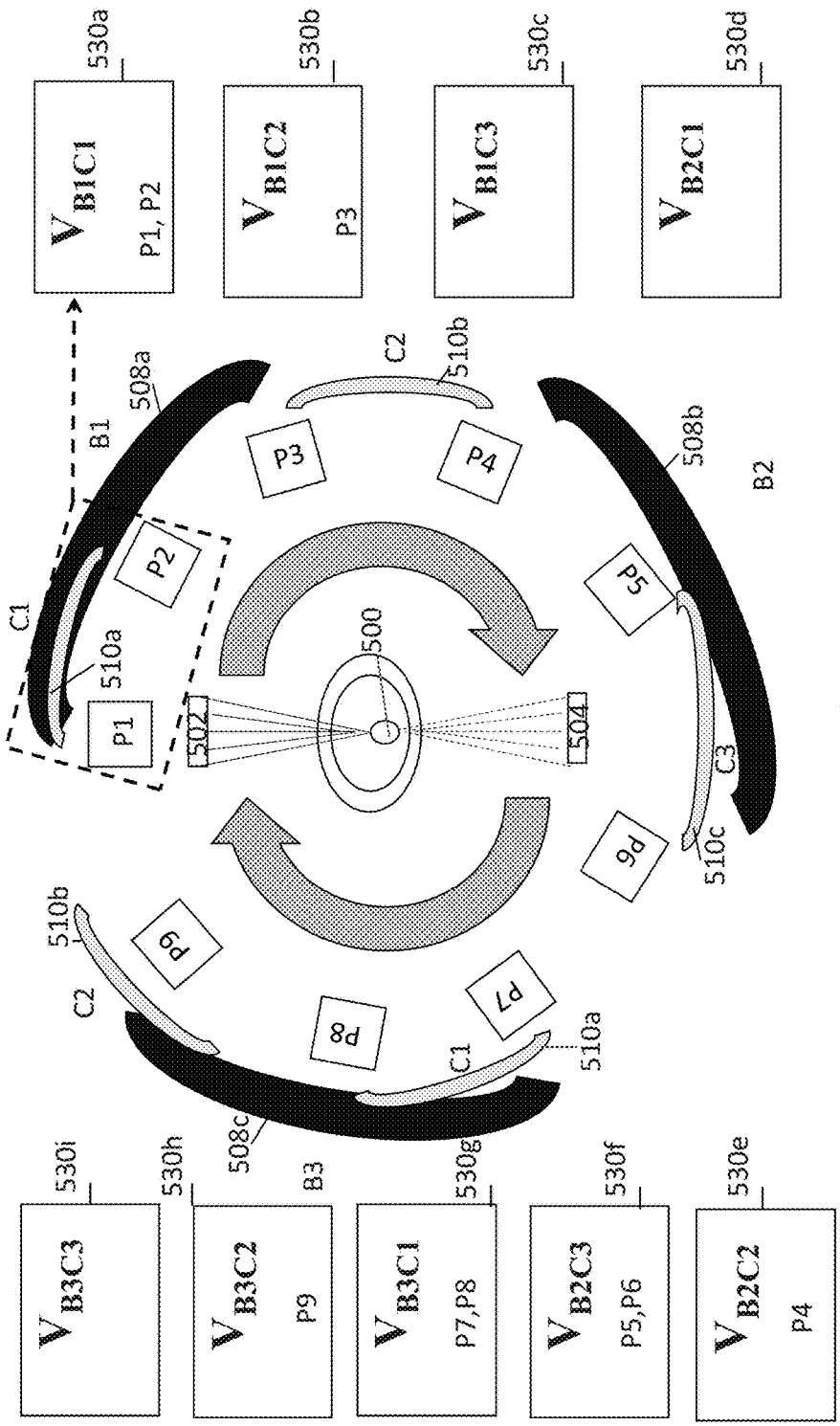
FIG. 5 illustrates an example technique for sorting projection images into respective combined bins in accordance with some embodiments.

More significant to the current invention(s), in order to generate volumetric images that take into account both the breathing motion and the cardiac motion of the patient, the projection images may also be sorted based on both the respiratory phase bins and the cardiac phase bins. FIG. 5 illustrates an embodiment of the example technique to sort the projection images into various combined phase bins that take both physiological cycles into account. As shown in FIG. 5, in order to obtain various projection images of the patient 500, the gantry comprising a radiation emitter 502, and detector 504 rotate around that patient 500, taking various projection images at various angles around the patient. In the illustrated embodiment, projection images P1-P9 are taken at varying angles as the gantry rotates around the patient. Of course, it should be appreciated that the illustrated embodiment is a simplified embodiment that generates 9 projection images as the gantry rotates fully around the patient for illustrative purposes only, but other embodiments may generate any number of projection images at any number of angles around the patient. Also, in other embodiments, several projection images may be generated at the same gantry angle.

In the illustrated embodiment, the processor (not shown in FIG. 5) also tracks one or more physiological cycles based on various markers, as discussed above. In the current example, both the breathing cycle and respiratory cycle are tracked by the processor, thereby identifying what part of the respective physiological cycle each projection image belongs to. As shown in the figure, it is determined that projection images P1, P2, and P3 are binned into breathing phase bin B1 (508a), whereas P4, P5 and P6 are binned into breathing phase bin B2 (508b), and P7, P8 and P9 are binned into breathing phase bin B3 (508c).

Similarly, projection images P1 and P2 may be binned into cardiac phase bin C1 (510a), P3 and P4 may be binned into cardiac phase bin C2 (510b), and P5 and P6 may be binned into cardiac phase bin C3 (510c). Thus since P1-P6 comprise a full cardiac cycle, the cardiac cycle repeats at P7, such that P7 and P8 are binned into C1 (510a), and P9 is binned into C2 (510b). As shown in the figure, the breathing cycle and the cardiac cycle may have different periods, such that some projection images belong to one physiological cycle, but not to another.

In order to construct volumetric images that account for both physiological cycles, the projection images are sorted into various combined phase bins (530a-530i). For example, projection images that correspond to both B1 and C1 may be combined to determine volumetric image $V_{B1C1}$. In the illustrated embodiment, projection images P1 and P2 belong both to breathing phase bin B1 (508a), and cardiac phase bin C1 (510a). Thus, P1 and P2 may be further binned into combined phase bin 530a, such that the projection images are used to construct $V_{B1C1}$. It should be noted, that projection image P3 belongs to B1, but not C1, and thus cannot be binned into 530a, but is instead binned into 530b. Projection image P3, along with other projection images in this combined phase bin 530b (not shown), may be used to construct volumetric image $V_{B1C2}$. In the illustrated embodiment, since there are three respiratory phase bins and three cardiac phase bins, a total of nine volumetric images are possible (i.e., $V_{B1C1}$, $V_{B1C2}$, $V_{B1C3}$, $V_{B2C1}$, $V_{B2C2}$, $V_{B2C3}$, $V_{B3C1}$, $V_{B3C2}$, $V_{B3C3}$). Of course, it should be appreciated that other embodiments may generate a larger or smaller number of total volumetric images, and the above example is presented for illustrative purposes only. Since the above simplified example is only concerned with 9 projection images, some combined bins in the illustrated embodiment do not have any projection images (e.g., combined phase bin 530c, combined phase bin 530d) that belong to both physiological cycles.

Regardless of how many projection images are in a particular combined phase bin 530, typically additional volumetric images are created for the combined phase bin to generate a more accurate and detailed volumetric image. Additional volumetric images may be determined using projection images that correspond to different combined phase bins through a deformable registration process that will be discussed in further detail below. These additional volumetric images may be used to determine a more accurate composite volumetric image for a particular phase bin (or combination of physiological phase bins).

In some embodiments, the act of determining the additional volumetric image may be performed using a processor (e.g., the processor 54). For example, an additional volumetric image for combined phase bin 530a ($V_{B1C1}$) may be determined using projection images from combined phase bin 530b or from combined phase bin 530c, or any other combined phase bin 530d-530i.

Figure 6:
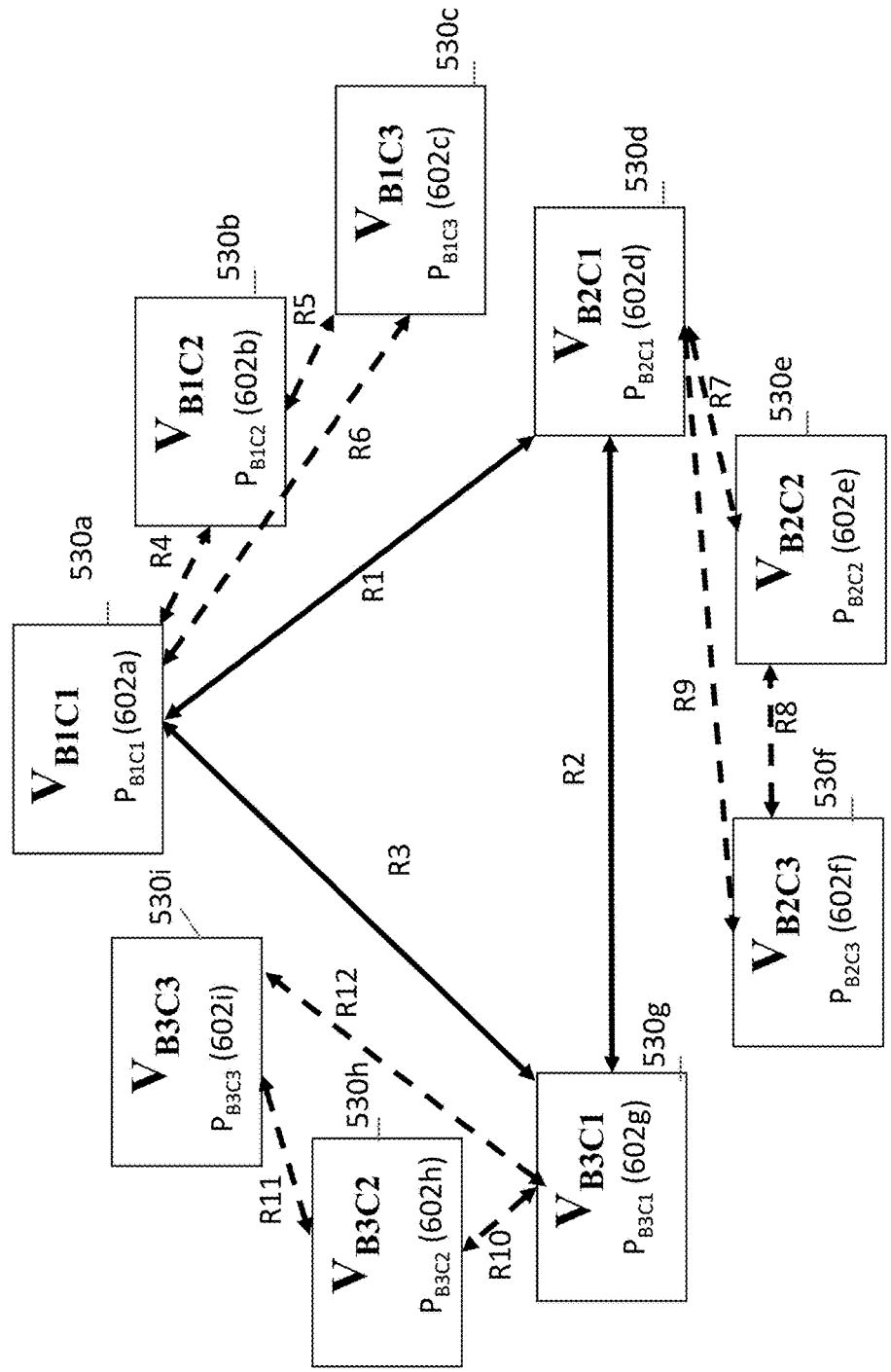
FIG. 6 illustrates a set of registrations determined between a plurality of combined phase bins in accordance with some embodiments.

FIG. 6 illustrates an example technique of determining additional volumetric images for each combined phase bin based on image registrations that are determined between one combined phase bin to another combined phase bin. The technique of FIG. 6 may be an example of the Item 204 in the method 200. The illustrated embodiment shows all nine combined phase bins (530a-530i) that contain projection images that belong both to a particular breathing phase bin and a particular cardiac phase bins. For example, projection images $P_{B1C1}$ (602a) that belong to both breathing phase bin B1, and cardiac phase bin C1 are binned into 530a; these projection images 602a are used to construct volumetric image $V_{B1C1}$. Similarly, each of the other combined phase bins 530b-530i each comprise respective projection images 602b-602i that denote projection images that belong to both the respective physiological phase bins.

In the illustrated embodiment, an initial volumetric image of a particular combined phase bin 530 is registered with its adjacent volumetric image of another combined phase bin that has at least one physiological phase bin in common. Thus, an image registration R1 may be determined between combined phase bin 530a and combined phase bin 530d because both combined phase bins correspond to the same cardiac phase bin C1. Similarly, an image registration R2 may be determined between combined phase bin 530d and combined phase bin 530g because both combined phase bins correspond to the same cardiac phase bin C1. Additionally, or alternatively, another image registration R3 may be determined directly between combined phase bin 530a and combined phase bin 530g because both combined phase bins correspond to C1.

Similarly, given that combined phase bin 530a, and combined phase bin 530b correspond to the same breathing phase bin B1, an image registration R4 may be determined between 530a and 530b. Another image registration R5 maybe determined between combined phase bin 530b and combined phase bin 530c. Additionally, or alternatively, another image registration R6 may be determined directly between 530a and 530c. Similarly, other image registrations R7-R12 may be similarly determined. It should be appreciated that many other combinations of image registrations may be similarly determined, and that illustrated embodiment only depicts a portion of all possible image registrations for illustrative purposes.

In some embodiments, each image registration R may be a deformation registration that represents a change between two adjacent volumetric images (e.g., volumetric image $V_{B1C1}$ constructed using projection images $P_{B1C1}$ 602a and volumetric image $V_{B2C1}$ constructed using projection images $P_{B2C1}$ 602d). For example, in some embodiments, the deformation registration may include a plurality of vectors that represent how different parts in one volumetric image are "deformed" to reach the configuration (e.g., size, shape, and/or position) of the corresponding parts in the adjacent volumetric image. In some embodiments, the determining of the registrations R may be performed by a processor (e.g., processor 54). Also, in some embodiments, the data regarding the registrations R may be stored in a non-transitory medium for later retrieval and/or processing. In further embodiments, the data regarding the registrations R may also be displayed in a screen (e.g., screen 56) for viewing by a user. Furthermore, in some embodiments the registration R are determined based on the projection images only (2D-2D registration) or based on volumetric image and projection set of image(s) (3D-2D registration).

Figure 7A:
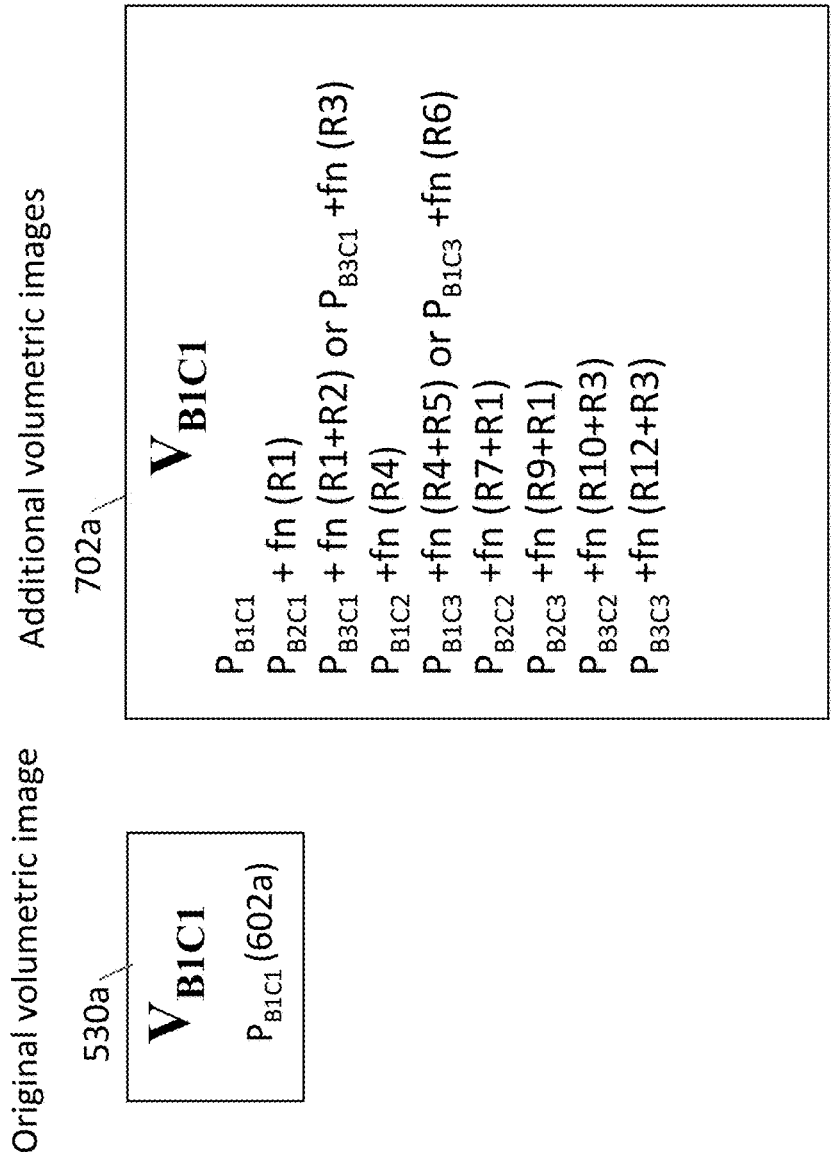
FIGS. 7A-7B illustrate a technique for obtaining additional volumetric images for two combined phase bins using the set of registrations illustrated in FIG. 6 in accordance with some embodiments.
Figure 7B:
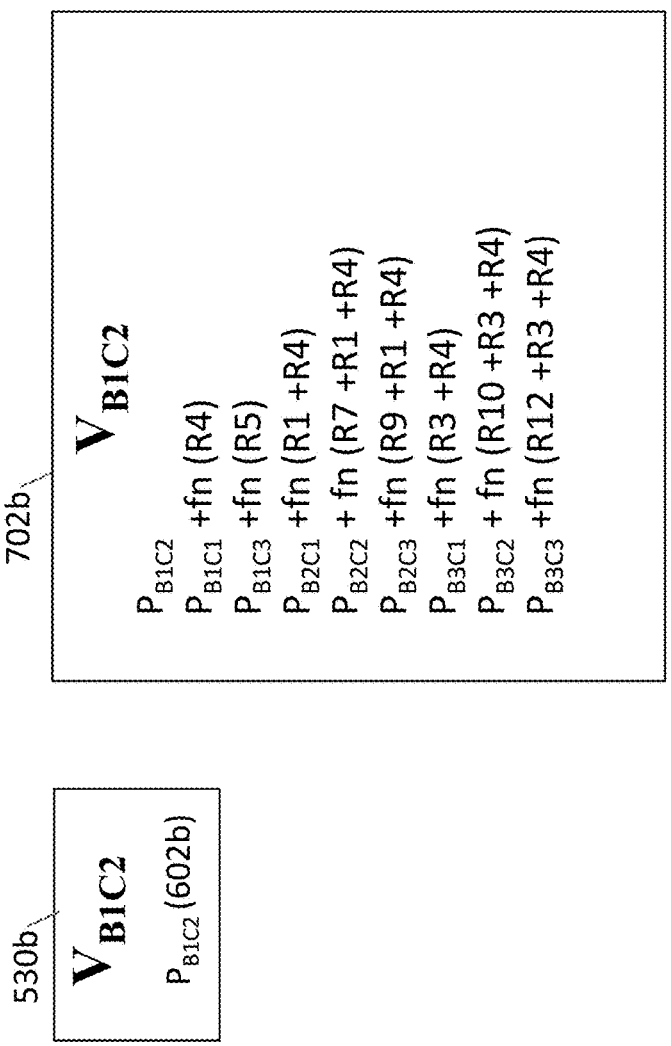

Referring now to FIGS. 7A-7D, an example technique of generating additional volumetric images for each combined phase bin based on the determined image registrations in FIG. 6 is illustrated. Turning first to FIG. 7A, projection images $P_{B1C1}$ 602a may be used to create an original volumetric image $V_{B1C1}$ for combined phase bin 530a. However, to create additional volumetric images for $V_{B1C1}$, additional projection images 702a from other combined phase bins may be used. Additional volumetric images for $V_{B1C1}$ may be generated using the existing projection images $P_{B1C1}$. Since projection images $P_{B1C1}$ belong to the right combination of phase bins, no registrations need to be applied to these projection images.

As shown in the figure, because the projection images that correspond to $P_{B2C1}$ are from a different phase bin combination (B2 and C1) than that of combined phase bin 530a, in order to use these projection images for constructing volumetric image $V_{B1C1}$, these projection images are modified using the registration R1. The modification is possible because the registration R1 provides information on how the two initial volumetric images ($V_{B1C1}$ and $V_{B2C1}$) differ from each other. Thus, a new volumetric image $V_{B1C1}$ may be created using projection images gathered from $P_{B2C1}$, and a function of the registration R1. It should be appreciated that the addition signs "+" in the figures do not signify actual addition of functions of the registrations, but simply denote that a function of a registration is utilized along with an image, or another image registration.

In some embodiments, the volumetric image $V_{B2C1}$ may be transformed by a deformation using registration R1 resulting in a deformed volumetric image to reach the configuration (e.g., size, shape, and/or position) of the volumetric image $V_{B1C1}$. A forward projection of the deformed volumetric image at the same gantry angles may then be performed to generate modified projection images. In one or more embodiments, modified projection images refer to projection images that have been transformed by an image registration. For example, projection image P4 that is transformed by a particular R may result in P4'. The modified projection images may then be used to form the additional volumetric image $V_{B1C1}$. For example, the modified projection images may be the only images used to construct the volumetric image $V_{B1C1}$. Alternatively, the modified projection images may be used with other projection images (e.g., projection images from the $P_{B1C1}$, and/or projection images from other combined phase bin(s)) to form the new volumetric image $V_{B1C1}$. In other embodiments, the registration R1 may be directly incorporated in the reconstruction of the volumetric image $V_{B1C1}$ without performing the intermediate act of determining modified projection images (which may obviate performing a forward projection and a back projection). In either one of the techniques, the original projection images $P_{B1C1}$ may be considered as being "used" to determine the new (additional) volumetric image $V_{B1C1}$.

As shown in 702a, another way to create additional volumetric images for $V_{B1C1}$, is to use projection images $P_{B3C1}$, and apply the relevant image registrations. As was the case with projection images $P_{B2C1}$, because the projection images corresponding to $P_{B3C1}$ are from a different phase bin combination (B3 and C1), in order to use these projection images for constructing the volumetric image $V_{B1C1}$, these projection images are modified using the registrations R1, R2. Note that both registrations R1, R2 are used for modifying the projection images $P_{B3C1}$ because the registration R2 provides information on how the volumetric image $V_{B3C1}$ is different from the volumetric image $V_{B2C1}$, but not how the volumetric image $V_{B3C1}$ is different from the volumetric image $V_{B1C1}$. Thus, in order to have sufficient information regarding how the volumetric image $V_{B3C1}$ is different from (or to be transformed to) the volumetric image $V_{B1C1}$ or vice versa, both registrations R1 and R2 are used. In another embodiment, rather than using both registrations R1 and R2, registration R3 may be used to determine how the volumetric image $V_{B3C1}$ is different from (or to be transformed to) the volumetric image $V_{B1C1}$.

Yet another way to create additional volumetric images for $V_{B1C1}$, is to utilize registration R4 to modify projection images $P_{B1C2}$. Image registration R4 contains information that transforms another volumetric image (e.g., volumetric image $V_{B1C2}$) into volumetric image $V_{B1C1}$. As shown in the figure, because the projection images corresponding to $P_{B1C2}$ are from a different combination of phase bins (B1 and C2), in order to use these volumetric images for constructing the volumetric image $V_{B1C1}$, they are modified using the registration R4.

Similarly, because volumetric image $V_{B1C3}$ is a volumetric image that corresponds to a different combination of phase bins (B1 and C3), in order to use these this volumetric image to create another volumetric image for volumetric image $V_{B1C1}$, image registrations R4 and R5 are used to modify the projection images $P_{B1C3}$. Alternatively, or additionally, volumetric image projection images $P_{B1C3}$ may be transformed to create additional volumetric images $V_{B1C1}$ using image registration R6 which contains information on how to modify volumetric image $V_{B1C3}$ into volumetric image $V_{B1C1}$.

Similarly, because volumetric image $V_{B2C2}$ is a volumetric image that corresponds to a different combination of phase bins (B2 and C2), in order to use these this volumetric image to create another volumetric image for volumetric image $V_{B1C1}$, image registrations R7 and R1 are used to modify the projection images $P_{B2C2}$.

Similarly, because volumetric image $V_{B2C3}$ is a volumetric image that corresponds to a different combination of phase bins (B2 and C3), in order to use these this volumetric image to create another volumetric image for volumetric image $V_{B1C1}$, image registrations R9 and R1 are used to modify the projection images $P_{B2C3}$.

Similarly, because volumetric image $V_{B3C2}$ is a volumetric image that corresponds to a different combination of phase bins (B3 and C2), in order to use these this volumetric image to create another volumetric image for volumetric image $V_{B1C1}$, image registrations R10 and R3 are used to modify the projection images $P_{B3C2}$.

Similarly, because volumetric image $V_{B3C3}$ is a volumetric image that corresponds to a different combination of phase bins (B3 and C3), in order to use these this volumetric image to create another volumetric image for volumetric image $V_{B1C1}$, image registrations R12 and R3 are used to modify the projection images $P_{B3C3}$.

As illustrated in the above example, additional volumetric images for $V_{B1C1}$ are determined using projection images from other combined phased bins. This provides more data from which to create volumetric images, thereby generating a more accurate and detailed volumetric image that can be used for diagnostic purposes.

In some embodiments, such a technique allows all of the projection images P1-P9 to be used for determining additional volumetric images for $V_{B1C1}$. In other embodiments, instead of using all of the projection images P1-P9, the determination of the additional volumetric image $V_{B1C1}$ may be achieved by using one or more of the projection images, that are less than all of the projection images, from each of the sets (phase bins).

In some embodiments, the same technique may be applied to determine additional volumetric images for other combined phase bins. For example, as shown in the FIG. 7B, in other embodiments, in addition to the original volumetric image constructed using projection images in combined phase bin 530b, additional volumetric images for $V_{B1C2}$ may be constructed using modified projection images 702b derived from other combined phase bins.

Additional volumetric images may be derived using the projection images $P_{B1C2}$ that correspond to both B1 and C2. As discussed above, these projection images need not be modified because they pertain to the same combined phase bin. However, when using projection images $P_{B1C1}$, these projection images are modified using image registration R4 that provides information on how the volumetric image $V_{B1C1}$ is different from (or to be transformed to) volumetric image $V_{B1C2}$, or vice versa. Also, when using projection images $P_{B1C3}$, these projection images are modified using image registration R5, which provides information on how the volumetric image $V_{B1C3}$ is different from (or to be transformed) to volumetric image $V_{B1C2}$, or vice versa.

Similarly, when using projection images $P_{B2C1}$, these projection images are modified using image registration R1 and R4, which together provide information on how the volumetric image $V_{B2C1}$ is different from (or to be transformed) to volumetric image $V_{B1C2}$, or vice versa.

Similarly, when using projection images $P_{B2C2}$, these projection images are modified using image registrations R7, R1 and R4, which together provide information on how the volumetric image $V_{B2C2}$ is different from (or to be transformed) to volumetric image $V_{B1C2}$, or vice versa.

Similarly, when using projection images $P_{B2C3}$, these projection images are modified using image registrations R9, R1 and R4, which together provide information on how the volumetric image $V_{B2C3}$ is different from (or to be transformed) to volumetric image $V_{B1C2}$, or vice versa.

Similarly, when using projection images $P_{B3C1}$, these projection images are modified using image registrations R3 and R4, which together provide information on how the volumetric image $V_{B3C1}$ is different from (or to be transformed) to volumetric image $V_{B1C2}$, or vice versa.

Similarly, when using projection images $P_{B3C2}$, these projection images are modified using image registrations R10, R3 and R4, which together provide information on how the volumetric image $V_{B3C2}$ is different from (or to be transformed) to volumetric image $V_{B1C2}$, or vice versa.

Similarly, when using projection images $P_{B3C3}$, these projection images are modified using image registrations R12, R3 and R4, which together provide information on how the volumetric image $V_{B3C3}$ is different from (or to be transformed) to volumetric image $V_{B1C2}$, or vice versa.

Similarly, the same technique (not shown) may be applied to determine additional volumetric images for $V_{B1C3}$, $V_{B2C1}$, $V_{B2C2}$, $V_{B2C3}$, $V_{B3C1}$, $V_{B3C2}$ and $V_{B3C3}$. The resulting sequence of new volumetric images created using the modified projection images may be considered modified or improved versions of the initial volumetric images constructed using projection images 602a-602i in combined phase bins 530-530i. As illustrated in the example, each of the volumetric images is determined (e.g., constructed) using all of the projection images P1-P9 from different combined phase bins. This is advantageous because it allows a full dose usage in the determination of the sequence of volumetric images. In other embodiments, one or more of the new volumetric images may be determined using one or more of the projection images, but not all, from each phase bin.

Also, in other embodiments, the projection images may be binned into different respective bins that are amplitude bins (instead of phase bins). For example, if a total amplitude range for a breathing cycle is 10 mm, then 3 amplitude bins may be prescribed that cover amplitude ranges 0-3.3 mm, 3.3-6.6 mm, 6.6-10 mm, respectively. Similarly, if a total amplitude range for a cardiac cycle is 3 mm, then 3 amplitude bins may be prescribed that cover amplitude ranges 0-1 mm, 1-2 mm, and 2-3 mm. In such cases, projection images that correspond to a particular combination of breathing and cardiac bins are generated when the breathing amplitudes are within the particular breathing amplitude range and the cardiac amplitudes are within the particular cardiac amplitude bin. In other embodiments, amplitudes are not used for the cardiac cycle. Instead, ECG is used to determine cardiac phases (e.g., by tracking the r-peak). In some embodiments, each of the volumetric images in the sequence may be determined (e.g., constructed) using all of the projection images P1-P9 from the different amplitude bins. In other embodiments, one or more of the new volumetric images may be determined using one or more of the projection images, but not all, from each amplitude bin. Also, instead of having equal sizes, in some embodiments, the amplitude ranges in the respective bins may be different from each other. In other embodiments, the amplitude ranges of the respective bins may overlap.

It should be noted that the types of bins that may be used with the method 200 are not limited to the phase bins and amplitude bins described in the above examples, and that other types of bins may be used in other embodiments.

In the above embodiments, the additional volumetric images are described as being for the same combined phase bin. In other embodiments, any of the additional volumetric images may be for a different combination of bins from those for the initial volumetric images. Following the above example, a new volumetric image may be constructed for a combination of bins B1-B2 and C1. In other words, the breathing phase range may be from, e.g., 100°-240° (i.e., between the phase ranges for breathing phase bins B1 and B2) and cardiac phase range may be C1. In such cases, the new volumetric image may be constructed using interpolation techniques on the registrations R1. It should be noted that a new volumetric image may be constructed for any arbitrary phase or phase ranges (or a combination of phase ranges) of one or more physiological cycles using interpolation techniques. Also, in some embodiments, via the same interpolation techniques, the processor may perform a deformation specifically for any projection image in order to consider residual motion within a bin.

In some embodiments, the modifying of the projection images may be performed using a processor (e.g., the processor 54). In some embodiments, the registrations R may be represented by respective matrices. In other embodiments, such as free form deformation, the representation may be more complex (e.g. involving b-splines). Also, in some embodiments, when two or more registrations R are involved in modifying a projection image, the processor may be configured to combine the registrations R. In some embodiments, the combination of registrations R may be a mathematical concatenation. In some embodiments, the processor may be configured to iteratively perform the multiplication or concatenation.

For example, to obtain a combined matrix for modifying the projection images P3, P4, P5 to construct a particular volumetric image, the processor may be configured to calculate a combined matrix by combining image registrations (e.g., through multiplication and addition) with each other. This results in the projection images being sequentially modified as additional registration R is being applied.

In the above embodiments, registrations R between adjacent images are combined. In other embodiments, the processor (e.g., processor 54) may be configured to replace each combination of registrations by the resulting deformation registration of the respective volumetric images (which are not adjacent). For example, the combined registration of R1, R9 may be replaced by the deformation registration between two volumetric images that do not have at least one phase bin in common (e.g., a registration between $V_{B1C1}$ and $V_{B2C3}$).

Also, in the above embodiments, modified projection images are generated using registration(s) R, and the modified projection images are then used to determine the new volumetric image. In other embodiments, the determination of the modified projection images is not required. For example, in other embodiments, the processor (e.g., the processor 54) may directly incorporate registration(s) R in the reconstruction of the new volumetric image(s) without performing the intermediate act of determining modified projection images (which may obviate performing a forward projection and a back projection).

In the above embodiments, each of the registrations R is obtained by processing volumetric images from one combined phase bin to another combined phase bin (e.g., volumetric images corresponding to two combined bins that have at least one phase bin in common). In other embodiments, one or more of the registrations R may be obtained by processing each of the initial volumetric images corresponding to the phase bin 530 with a reference image.

Figure 8A:
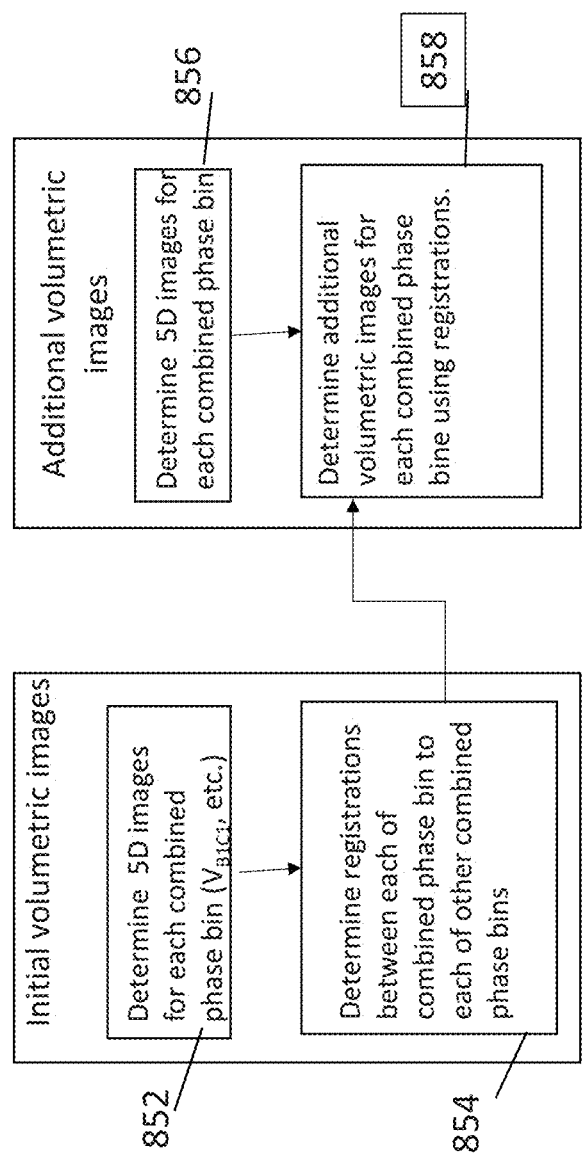
FIGS. 8A and 8B illustrates another technique for obtaining additional volumetric images between the plurality of combined phase bins in accordance with some embodiments.

FIG. 8A illustrates a technique of determining a volumetric image that involves using image registration in other embodiments. The technique of FIG. 8A may be another example of the Item 204 in the method 200. At 852, initial volumetric images for each of the combined phase bins ($V_{B1C1}$, $V_{B1C2}$, etc.) are determined. At 854, registrations are determined between each of the initial volumetric images for a particular combined phase bin, to each of the other initial volumetric images, as will be described in further detail in FIG. 8B. At 856, in order to determined additional volumetric images, initial volumetric images for the combined phase bins are gathered. At 858, the registrations determined in step 854 are applied on the gathered initial volumetric images to determined additional volumetric images for each of the combined phase bins.

Figure 8B:
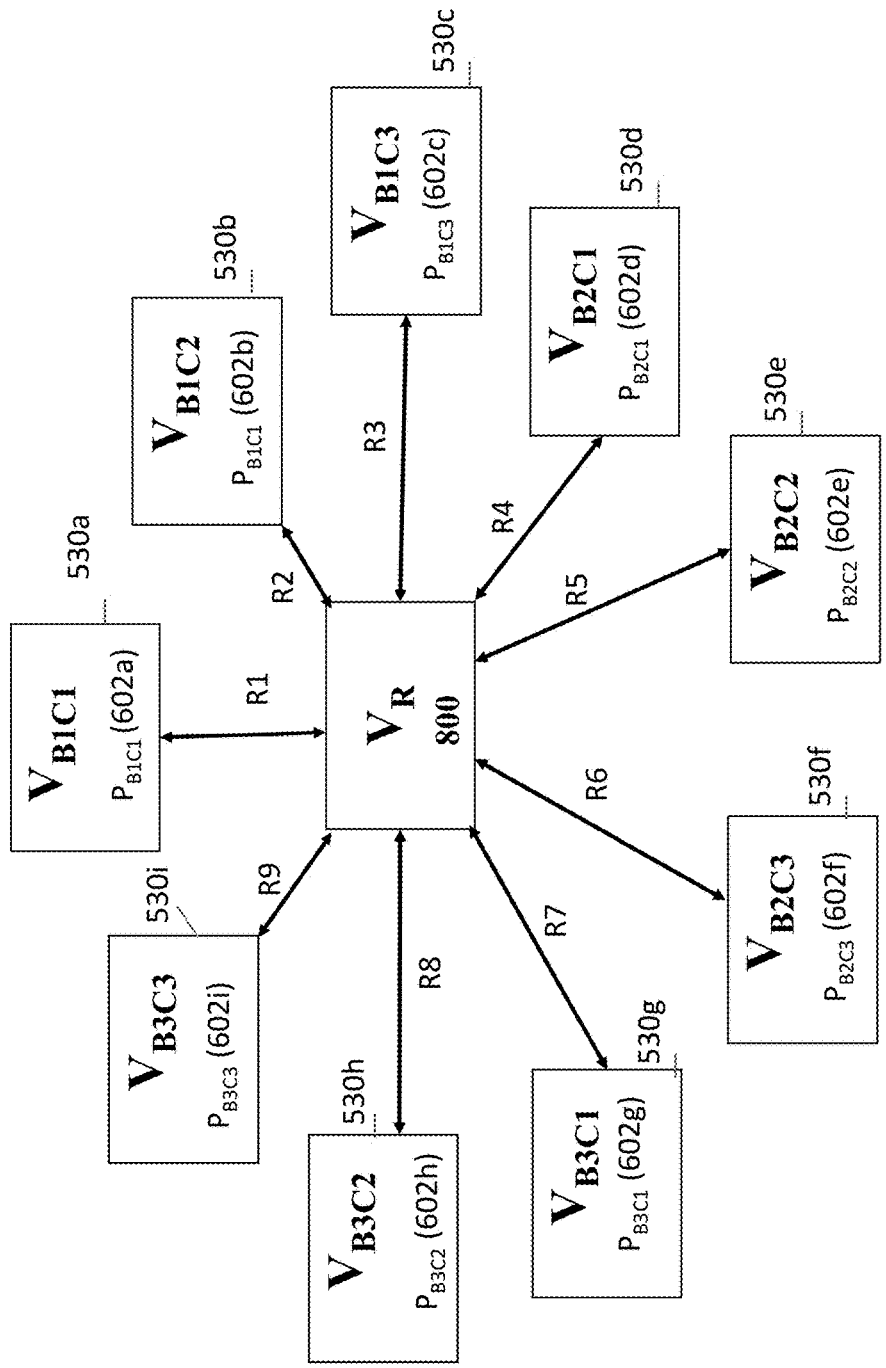

This concept is illustrated in detail in FIG. 8B. In the illustrated embodiments, each of the initial volumetric images corresponding to combined phase bins 530a-530i is registered with a reference volumetric image $V_R$ 800. Thus, an image registration R1 may be determined between volumetric images $V_{B1C1}$, $V_R$, an image registration R2 may be determined between volumetric images $V_{B1C2}$, $V_R$, an image registration R3 may be determined between volumetric images $V_{B1C3}$, $V_R$, an image registration R4 may be determined between volumetric images $V_{B2C1}$, $V_R$, an image registration R5 may be determined between volumetric images $V_{B2C2}$, $V_R$, an image registration R6 may be determined between volumetric images $V_{B2C3}$, $V_R$, an image registration R7 may be determined between volumetric images $V_{B3C1}$, $V_R$, an image registration R8 may be determined between volumetric images $V_{B3C2}$, $V_R$, and an image registration R9 may be determined between volumetric images $V_{B3C3}$ and $V_R$.

In some embodiments, each image registration R may be a deformation registration that represents a change between the two volumetric images (e.g., between $V_{B1C1}$ and $V_R$, or between $V_R$ and $V_{B1C2}$). For example, in some embodiments, the deformation registration may include a plurality of vectors that represent how different parts in one volumetric image are "deformed" to reach the configuration (e.g., size, shape, and/or position) of the corresponding parts in the reference image $V_R$ 800, or vice versa. In some embodiments, the determining of the registrations R may be performed by a processor (e.g., processor 54). Also, in some embodiments, the data regarding the registrations R may be stored in a non-transitory medium for later retrieval and/or processing. In further embodiments, the data regarding the registrations R may also be displayed in a screen (e.g., screen 56) for viewing by a user.

In some embodiments, the reference image $V_R$ 800 may be a volumetric image that was pre-determined, such as from a previous imaging session. In other embodiments, the reference image $V_R$ 800 may be any one of the volumetric images constructed using projection images in the combined phase bins 530a-530i. Also, in some embodiments, the reference image $V_R$ 800 may be arbitrarily selected from the volumetric images created using projection images in the combined phase bins 530a-530i. In other embodiments, the reference image $V_R$ 800 may be selected based on any other criteria.

Figure 9:
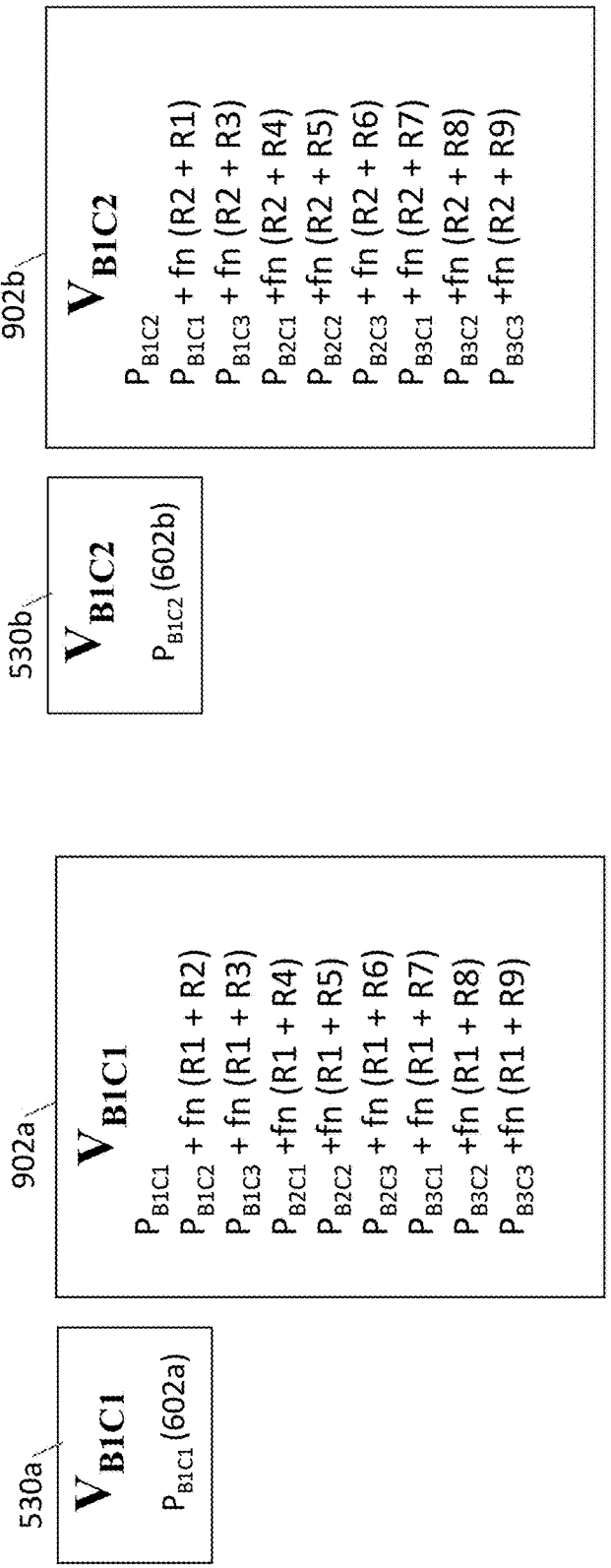
FIG. 9 illustrates another technique for obtaining additional volumetric images for two combined phase bin using the set of registrations illustrated in FIG. 8B in accordance with some embodiments.

These determined registration(s) R may be used to determine additional volumetric images for each of the combined phase bins 530a-530i. As shown in FIG. 9, a new volumetric image for $V_{B1C1}$ may be determined using modified projection images 902a from any other combined phase bin and the determined registrations R of FIG. 8. In particular, because the volumetric image $V_{B1C1}$ is for the same combined phase bin, projection images $P_{B1C1}$ may be used to construct the additional volumetric image without any modification.

On the other hand, because the projection images $P_{B1C2}$ correspond to a different combination of physiological bins (B1 and C2), in order to use projection images from B1 and C2 for constructing the volumetric image, these projection images are modified using the registrations R1, R2. Note that both registrations R1, R2 are used for modifying the projection images because the registration R2 provides information on how the volumetric image $V_{B1C1}$ is different from the reference volumetric image $V_R$ 800, but not how the reference image $V_R$ 800 is different from the volumetric image $V_{B1C2}$. Thus, in order to have sufficient information regarding how the volumetric image $V_{B1C1}$ is different from (or to be transformed to) the volumetric image $V_{B1C2}$, or vice versa, both registrations R1, R2 are used.

Similarly, because the projection images $P_{B1C3}$ correspond to a different combination of phase bins (B1 and C3), in order to use projection images from B1 and C3 for constructing the volumetric image $V_{B1C1}$, these projection images are modified using the registrations R1, R3. Note that both registrations R1, R3 are used for modifying the projection images because the registration R3 provides information on how the volumetric image $V_{B1C1}$ is different from the reference volumetric image $V_R$ 800, but not how the reference image $V_R$ 800 is different from the volumetric image $V_{B1C3}$. Thus, in order to have sufficient information regarding how the volumetric image $V_{B1C3}$ is different from (or to be transformed to) the volumetric image $V_{B1C1}$, or vice versa, both registrations R1, R3 are used.

Similarly, because the projection images $P_{B2C1}$ correspond to a different combination of phase bins (B2 and C1), in order to use projection images from B2 and C3 for constructing the volumetric image $V_{B1C1}$, these projection images are modified using the registrations R1, R4. Note that both registrations R1, R4 are used for modifying the projection images because the registration R4 provides information on how the volumetric image $V_{B2C1}$ is different from the reference volumetric image $V_R$ 800, but not how the reference image $V_R$ 800 is different from the volumetric image $V_{B2C1}$. Thus, in order to have sufficient information regarding how the volumetric image $V_{B2C1}$ is different from (or to be transformed to) the volumetric image $V_{B1C1}$, or vice versa, both registrations R1, R4 are used.

Similarly, because the projection images $P_{B2C2}$ correspond to a different combination of phase bins (B2 and C2), in order to use projection images from B2 and C2 for constructing the volumetric image $V_{B1C1}$, these projection images are modified using the registrations R1, R5. Note that both registrations R1, R5 are used for modifying the projection images because the registration R5 provides information on how the volumetric image $V_{B1C1}$ is different from the reference volumetric image $V_R$ 800, but not how the reference image $V_R$ 800 is different from the volumetric image $V_{B2C2}$. Thus, in order to have sufficient information regarding how the volumetric image $V_{B2C2}$ is different from (or to be transformed to) the volumetric image $V_{B1C1}$, or vice versa, both registrations R1, R5 are used.

Similarly, because the projection images $P_{B2C3}$ correspond to a different combination of phase bins (B2 and C3), in order to use projection images from B2 and C3 for constructing the volumetric image $V_{B1C1}$, these projection images are modified using the registrations R1, R6. Note that both registrations R1, R6 are used for modifying the projection images because the registration R6 provides information on how the volumetric image $V_{B1C1}$ is different from the reference volumetric image $V_R$ 800, but not how the reference image $V_R$ 800 is different from the volumetric image $V_{B2C3}$. Thus, in order to have sufficient information regarding how the volumetric image $V_{B2C3}$ is different from (or to be transformed to) the volumetric image $V_{B1C1}$, or vice versa, both registrations R1, R6 are used.

Similarly, because the projection images $P_{B3C1}$ correspond to a different combination of phase bins (B3 and C1), in order to use projection images from B3 and C1 for constructing the volumetric image $V_{B1C1}$, these projection images are modified using the registrations R1, R7. Note that both registrations R1, R7 are used for modifying the projection images because the registration R7 provides information on how the volumetric image $V_{B1C1}$ is different from the reference volumetric image $V_R$ 800, but not how the reference image $V_R$ 800 is different from the volumetric image $V_{B3C1}$. Thus, in order to have sufficient information regarding how the volumetric image $V_{B3C1}$ is different from (or to be transformed to) the volumetric image $V_{B1C1}$, or vice versa, both registrations R1, R7 are used.

Similarly, because the projection images $P_{B3C2}$ correspond to a different combination of phase bins (B3 and C2), in order to use projection images from B3 and C2 for constructing the volumetric image $V_{B1C1}$, these projection images are modified using the registrations R1, R8. Note that both registrations R1, R8 are used for modifying the projection images because the registration R8 provides information on how the volumetric image $V_{B1C1}$ is different from the reference volumetric image $V_R$ 800, but not how the reference image $V_R$ 800 is different from the volumetric image $V_{B3C2}$. Thus, in order to have sufficient information regarding how the volumetric image $V_{B3C2}$ is different from (or to be transformed to) the volumetric image $V_{B1C1}$, or vice versa, both registrations R1, R8 are used.

Similarly, because the projection images $P_{B3C3}$ correspond to a different combination of phase bins (B3 and C3), in order to use projection images from B3 and C3 for constructing the volumetric image $V_{B1C1}$, these projection images are modified using the registrations R1, R9. Note that both registrations R1, R9 are used for modifying the projection images because the registration R9 provides information on how the volumetric image $V_{B1C1}$ is different from the reference volumetric image $V_R$ 800, but not how the reference image $V_R$ 800 is different from the volumetric image $V_{B3C3}$. Thus, in order to have sufficient information regarding how the volumetric image $V_{B3C3}$ is different from (or to be transformed to) the volumetric image $V_{B1C1}$, or vice versa, both registrations R1, R9 are used.

In some embodiments, the same technique may be applied to determine additional volumetric images for other combined phase bins (i.e., $V_{B1C2}$, $V_{B1C3}$, etc.). For example, as shown in the figure, in other embodiments, another new volumetric image for $V_{B1C2}$ may be constructed using modified projection images 902b. In the illustrated example, additional volumetric image $V_{B1C2}$ may also be created using projection images in other combination of bins by using the respective image registration. In the illustrated examples, modified projection images from phase bin combination B1 and C1 are obtained by using a combination of the registrations R1, R2, which provides information on how the volumetric image $V_{B1C2}$ is different from (or to be transformed to) the volumetric image $V_{B1C1}$, or vice versa. Also, the modified projection images $P_{B1C3}$ from phase bin combination B1 and C3 are obtained by using a combination of the registrations R2, R3, which provides information on how the volumetric image $V_{B1C3}$ is different from (or to be transformed to) the volumetric image $V_{B1C2}$, or vice versa. The projection images $P_{B2C1}$ are modified by using the combination of registrations R2, R4, which provides information on how the volumetric image $V_{B2C1}$ is different from (or to be transformed to) the volumetric image $V_{B1C2}$, or vice versa. Similarly, the projection images $V_{B2C2}$ are modified by using the combination of registrations R2, R5, which provides information on how the volumetric image $V_{B2C2}$ is different from (or to be transformed to) the volumetric image $V_{B1C2}$, or vice versa. Similarly, the projection images $P_{B2C3}$ are modified by using the combination of registrations R2, R6, which provides information on how the volumetric image $V_{B2C3}$ is different from (or to be transformed to) the volumetric image $V_{B1C2}$, or vice versa. Similarly, the projection images $P_{B3C1}$ are modified by using the combination of registrations R2, R7, which provides information on how the volumetric image $V_{B3C1}$ is different from (or to be transformed to) the volumetric image $V_{B1C2}$, or vice versa. Similarly, the projection images $P_{B3C2}$ are modified by using the combination of registrations R2, R8, which provides information on how the volumetric image $V_{B3C2}$ is different from (or to be transformed to) the volumetric image $V_{B1C2}$, or vice versa. Similarly, the projection images $P_{B3C3}$ are modified by using the combination of registrations R2, R9, which provides information on how the volumetric image $V_{B3C3}$ is different from (or to be transformed to) the volumetric image $V_{B1C2}$, or vice versa.

The same technique may be applied to determine new volumetric images for each of the combined phase bins 530c-530i (not shown). As illustrated in the example, each of the additional volumetric images is determined (e.g., constructed) using all of the projection images P1-P9 from the different combined phase bins. This is advantageous because it allows a full dose usage in the determination of the sequence of volumetric images. In other embodiments, one or more of the new volumetric images may be determined using one or more of the projection images, but not all, from each set (e.g., phase bin).

In the above embodiments, modified projection images are generated using registration(s) R, and the modified projection images are then used to determine the new volumetric image. In other embodiments, the determination of the modified projection images is not required. For example, in other embodiments, the processor (e.g., the processor 54) may directly incorporate registration(s) R in the reconstruction of the new volumetric image(s) without performing the intermediate act of determining modified projection images (which may obviate performing a forward projection and a back projection).

As illustrated in the above example, the embodiments of the technique of FIG. 9 are advantageous because the determination of each of the new volumetric images does not involve using more than two registrations R.

In one or more embodiments, instead of determining registrations between $V_R$ and each of the initial volumetric images, a single registration may be determined from a first initial volumetric image to a second initial volumetric image. For example, a registration R1 may be determined directly between $V_{B1C1}$ and $V_{B1C2}$ such that projection images $P_{B1C2}$ need only be modified using R. Similarly, direct registrations may be determined between any of the combined phase bins. This alternate technique may be advantageous because the additional volumetric images are determined using only one registration R.

In the above embodiments, projection images P that spread across a complete phase range (e.g., 0°-360°) of the physiological cycle (or a combination of physiological cycles) are used to construct each new volumetric image. In other embodiments, instead of using projection images P from a complete phase range, projection images P from at least 50% of the complete phase range of the physiological cycle may be used. For example, in other embodiments, the volumetric image may be constructed using projection images from a partial set of the combined phase bins (e.g., from a combination of B1-B2 with C2-C3, etc.). Also, in other embodiments, the additional volumetric image may be constructed using projection images from only a partial number of combined phase bins (e.g., two other combined phase bins). For example, in other embodiments, the additional volumetric image may be constructed from projection images corresponding to combined phase bins that are separated by a phase range that is at least 25% of a complete phase range for the physiological cycle. In further embodiments, instead of using projection images P from a complete phase range, projection images P from at least 90% of the complete phase range of the physiological cycle may be used. It should be appreciated that the same techniques discussed above may be similarly applied to amplitude bins rather than phase bins in some embodiments.

It should be noted that the types of bins that may be used with the method 200 are not limited to the phase bins and amplitude bins described in the above examples, and that other types of bins may be used in other embodiments.

Figure 10A:
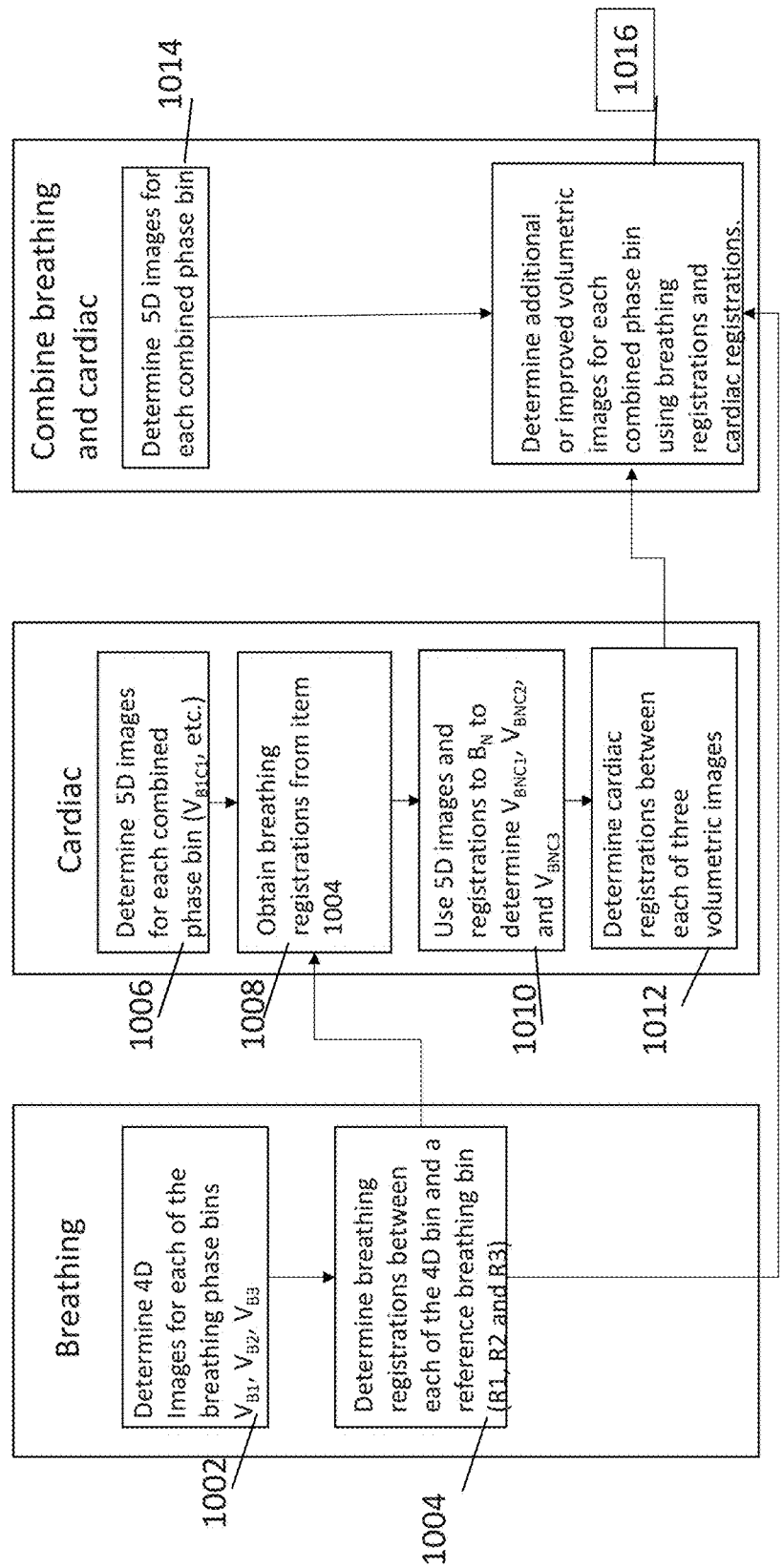
FIGS. 10A-10D illustrate another technique for obtaining additional volumetric images between the plurality of combined phase bins in accordance with some embodiments.

Referring now to FIG. 10A, an exemplary method of determining additional volumetric images for each combined phase bin is illustrated. In this example method, in the first column, registrations for a first physiological cycle (e.g., breathing cycle) are determined. Then, as illustrated in the second column, these registrations are used to determined registrations for the second physiological cycle (e.g., cardiac cycle). Finally, as illustrated in the third column, both these registrations are then used to determine additional volumetric images for each of the combined phase bins.

Figure 10B:
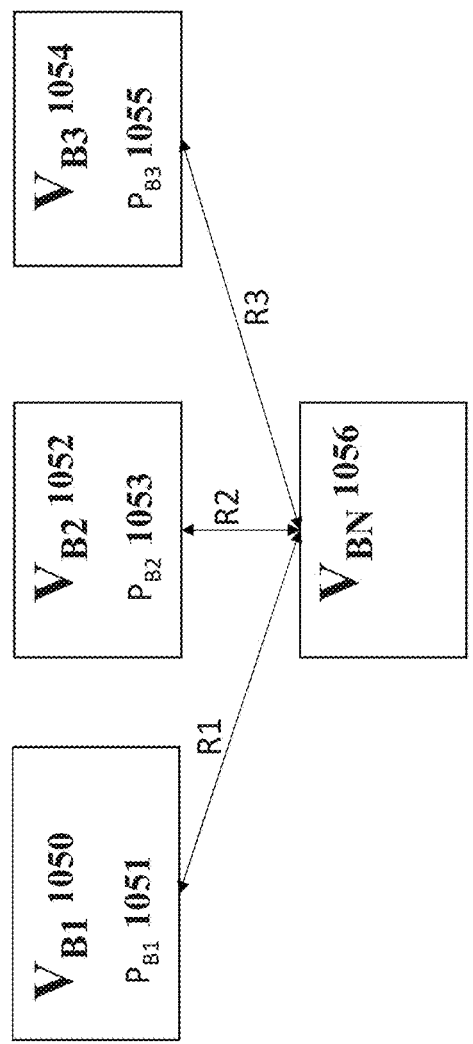

More specifically, at 1002, 4D images for each of the breathing bins are determined. At 1004, registrations are determined between each of the breathing bins and a reference breathing bin $B_N$ that is associated with a reference volumetric image 1056. The reference volumetric image 1056 may be generated during a treatment planning process, during a patient setup, or during a simulation process. FIG. 10B illustrates the concept of item 1004 with the example discussed previously. As shown in FIG. 10B, $P_{B1}$ (1051), $P_{B2}$ (1053) and $P_{B3}$ (1055) are utilized to create initial volumetric images $V_{B1}$ (1050), $V_{B2}$ (1052), $V_{B3}$ (1054), respectively. In step 1004, deformable registrations (R1, R2, and R3) are determined between $V_{B1}$ 1050 and $V_{BN}$ 1056, $V_{B2}$ 1052 and $V_{BN}$ 1056, and $V_{B3}$ 1054 and $V_{BN}$ 1056 (the reference volumetric image) respectively.

Referring back to FIG. 10A, at 1006, for each of the combined phase bins, volumetric images may be determined (e.g., $V_{B1C1}$, $V_{B2C2}$, etc.). In the example, there are three breathing phases B1, B2, B3, and three cardiac phases C1, C2, C3. Thus, nine volumetric images will be constructed for the different combinations of breathing-cardiac phases.

At 1008, the determined breathing registrations from step 1004 are gathered. At 1010, the breathing registrations are used to determine volumetric images for $V_{BNC1}$ (1060), $V_{BNC2}$ (1062), and $V_{BNC3}$ (1064). The volumetric images 1060, 1062, 1064 are cardiac correlated because each of them is for a certain cardiac phase. In the example, volumetric image 1060 is for cardiac phase C1, volumetric image 1062 is for cardiac phase C2, and volumetric image 1064 is for cardiac phase C3. It should be appreciated that $V_{BNC1}$ (1060) may be created by using deformation registration R1 on projection images $P_{B1C1}$. It may also be created by using deformation registration R2 on projection images $P_{B2C1}$. It may also be created by using deformation registration R3 on projection images $P_{B3C1}$.

Similarly, $V_{BNC2}$ (1062) may be created by using deformation registration R1 on projection images $P_{B1C2}$. It may also be created by using deformation registration R2 on projection images $P_{B2C2}$. It may also be created by using deformation registration R3 on projection images $P_{B3C2}$.

Similarly, $V_{BNC3}$ (1064) may be created by using deformation registration R1 on projection images $P_{B1C3}$. It may also be created by using deformation registration R2 on projection images $P_{B2C3}$. It may also be created by using deformation registration R3 on projection images $P_{B3C3}$.

Figure 10C:
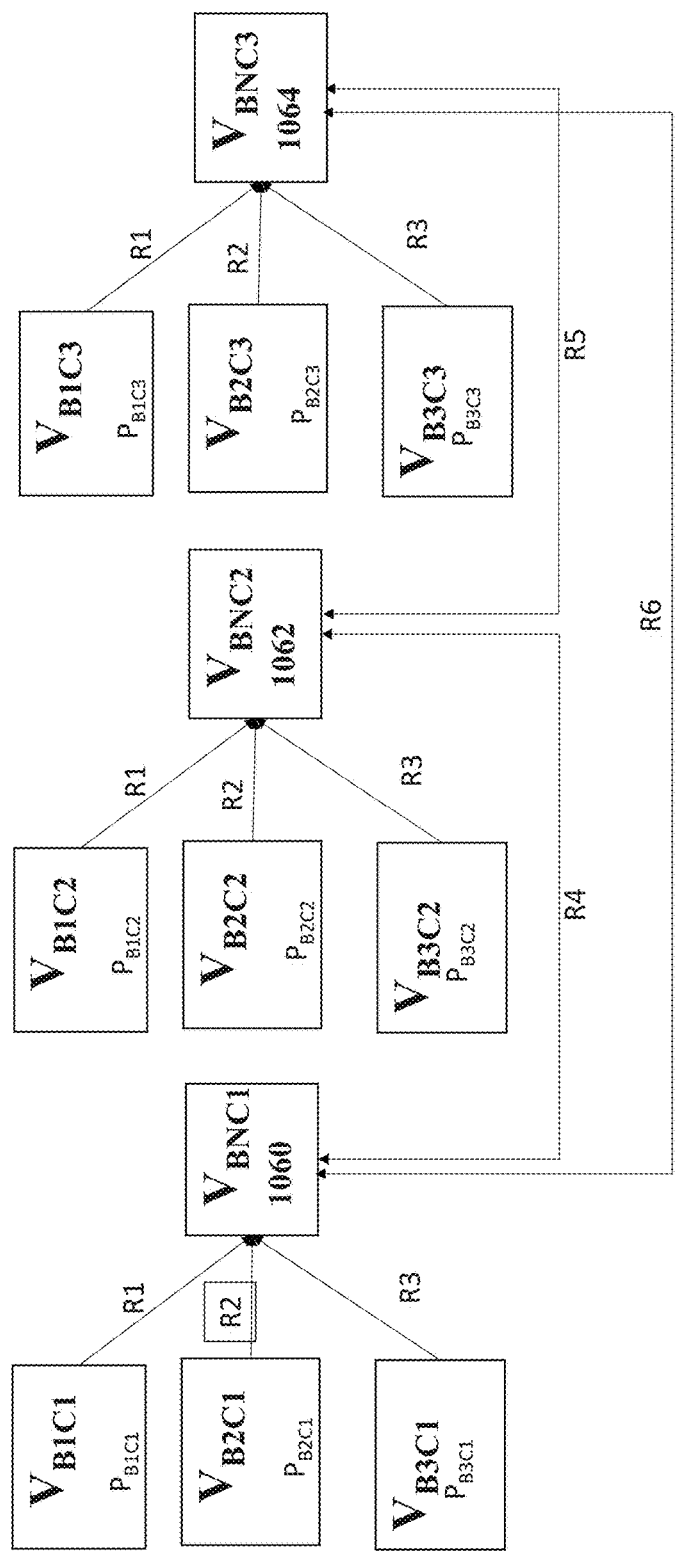

At 1012, these volumetric images are used to determine cardiac registrations between $V_{BNC1}$, $V_{BNC2}$ and $V_{BNC3}$. FIG. 10C illustrates this concept. As shown in FIG. 10C, the volumetric images ($V_{BNC1}$ 1060, $V_{BNC2}$ 1062, and $V_{BNC3}$ 1064) are utilized to determine the cardiac registrations. For example, deformable registration R4 may be determined between $V_{BNC1}$ 1060 and $V_{BNC2}$ 1062. Similarly, deformable registration R5 may be determined between $V_{BNC2}$ 1062 and $V_{BNC3}$ 1064. Similarly, deformable registration R6 may be determined between $V_{BNC1}$ 1060 and $V_{BNC3}$ 1064.

Figure 10D:
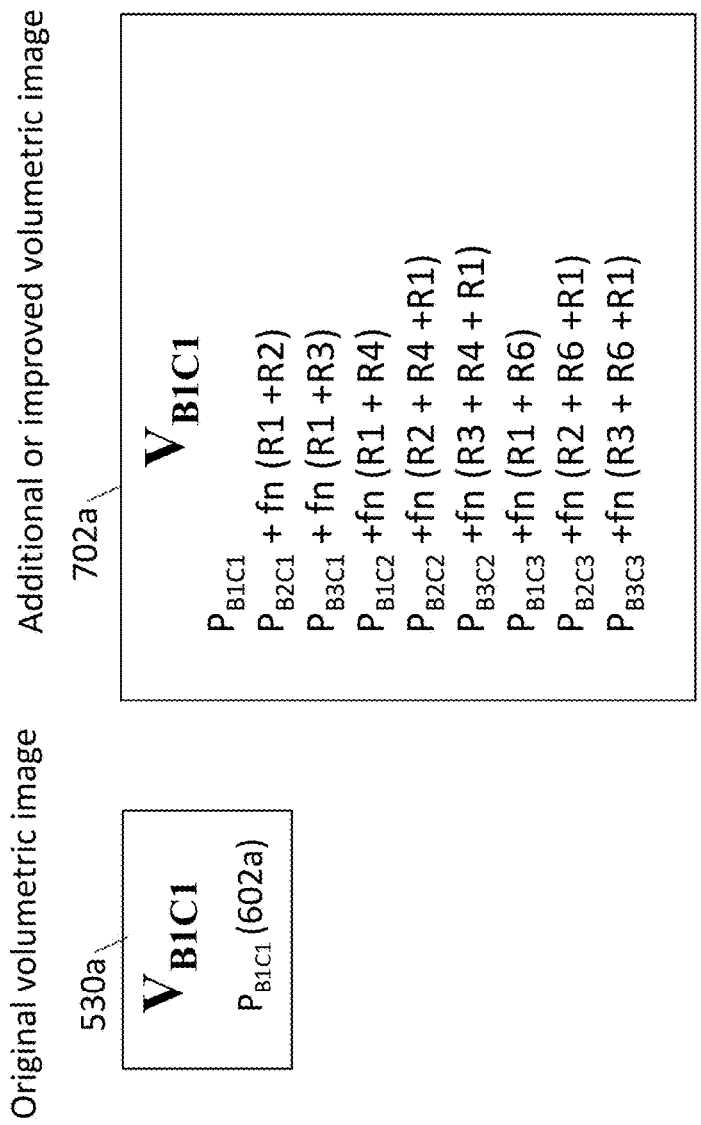

Referring back to FIG. 10A, now since both breathing registrations and cardiac registrations have been determined, they can be combined together to determined additional volumetric images for each of the combined phase bin. At 1014, for each of the combined phase bins, initial volumetric images may be determined (e.g., $V_{B1C1}$, $V_{B2C2}$, etc.). At 1016, both the breathing registrations and cardiac registrations may be used to determined additional volumetric images for each combined phase bin. Referring now to FIG. 10D, an exemplary method to determine additional/improved volumetric image 702a for $V_{B1C1}$ is illustrated.

These determined registration(s) R may be used to determine additional volumetric images for each of the combined phase bins 530a-530i. As shown in FIG. 10D, a new or improved volumetric image for $V_{B1C1}$ may be determined using modified projection images from any other combined phase bin and the determined registrations R of FIG. 10C. In particular, because the volumetric image $V_{B1C1}$ is for the same combined phase bin, projection images $P_{B1C1}$ for the original volumetric image may be used to construct the additional or improved volumetric image without any modification.

On the other hand, because the projection images $P_{B2C1}$ correspond to a different combination of physiological bins (B2 and C1), in order to use projection images from B2 and C1 for constructing the improved volumetric image, these projection images are modified using the registrations R1, R2. Similarly, because the projection images $P_{B3C1}$ correspond to a different combination of physiological bins (B3 and C1), in order to use projection images from B3 and C1 for constructing the volumetric image, these projection images are modified using the registrations R1, R3.

Similarly, because $P_{B1C2}$ correspond to a different combination of physiological bins (B1 and C2), in order to use projection images from B1 and C2 for constructing the volumetric image, these projection images are modified using the registrations R1, R4. Similarly, because $P_{B2C2}$ correspond to a different combination of physiological bins (B2 and C2), in order to use projection images from B2 and C2 for constructing the volumetric image, these projection images are modified using the registrations R2, R4, R1. Similarly, because $P_{B3C2}$ correspond to a different combination of physiological bins (B3 and C2), in order to use projection images from B3 and C2 for constructing the volumetric image, these projection images are modified using the registrations R3, R4, R1.

Similarly, because $P_{B1C3}$ correspond to a different combination of physiological bins (B1 and C3), in order to use projection images from B1 and C3 for constructing the volumetric image, these projection images are modified using the registrations R1, R6. Similarly, because $P_{B2C3}$ correspond to a different combination of physiological bins (B2 and C3), in order to use projection images from B2 and C3 for constructing the volumetric image, these projection images are modified using the registrations R2, R6, R1. Similarly, because $P_{B3C3}$ correspond to a different combination of physiological bins (B3 and C3), in order to use projection images from B3 and C3 for constructing the volumetric image, these projection images are modified using the registrations R3, R6, R1.

It should be appreciated that additional volumetric images may be determined for each of the combined phase bins similar to the example illustrated above.

It should be noted that although a reference breathing bin BN is utilized in the above example for illustrative purposes, other embodiments may simply determine registrations from one breathing bin to another breathing bin without using a reference breathing bin. For example, registrations between adjacent breathing bins (adjacent in phase) may be determined. In such cases, one arbitrary breathing bin may be chosen as reference for item 1010. Also, in some cases, the registration might be performed independently or within a single registration that may include prior knowledge (e.g., cyclic behavior).

The above technique is advantageous because it results in an improved volumetric image for a certain breathing stage and for a certain cardiac stage using projection image data associated with other different breathing stages and other cardiac stages (i.e., projection image data that wouldn't have been used). In some cases, the improved volumetric image is generated using at least 50%, and more preferably at least 75%, and even more preferably at least 90% (e.g., 100%), of the available projection images, wherein the projection images are generated while the subject is undergoing different breathing stages and cardiac stages.

Also, in some embodiments, the processing unit for carrying out the technique described with reference to FIG. 10A may include different components for carrying out different functions. For example, the processing unit may include (1) a first volumetric image generator to perform item 1002 (e.g., to reconstruct volumetric images using projection images from their respective breathing phase bins), (2) a first registration engine configured to perform item 1004 (e.g., to determine registrations of images with respect to breathing (breathing correlated images), wherein the registrations may be 2D-2D registrations, 3D-3D registrations, or 2D-3D registrations), (3) a second volumetric image generator (breathing-cardiac image generator) to perform item 1006 (e.g., to construct breathing-cardiac images for the different combinations of breathing-cardiac stages), (4) a third volumetric image generator (cardiac correlated image generator) for performing item 1010 (e.g., to construct cardiac correlated images, which may be 2D or 3D images), (5) a second registration engine configured to perform item 1012 (e.g., to determine registrations of cardiac correlated images, wherein the registrations may be 2D-2D registrations, 3D-3D registrations, or 2D-3D registrations), and (6) a fourth volumetric image generator for performing item 1016 (e.g., to determine additional or improved volumetric image(s) using the registrations of breathing correlated images and the registrations of cardiac correlated images.

In some cases, two or more of the components described above may be combined. For example, two or more of: the first volumetric image generator, the second volumetric image generator, the third volumetric image generator, and the fourth volumetric image generator, may be combined and may be implemented as an image generator. Thus, the term "image generator" may refer to a sub-image generator that is a part of an image generator, or may refer to an image generator that has sub-image generators.

Also, in some cases, a display may be provided that is communicatively coupled to the processing unit for displaying various information. For example, the processing unit may be configured to output signals for causing the display to display a graphic, which graphic may indicate or represent one or more volumetric images (or a subset of one of such volumetric image—i.e., a 2D cross sectional of a volumetric image) generated by the first volumetric image generator, breathing-cardiac images generated by the breathing-cardiac image generator, cardiac correlated images generated by the cardiac correlated images, volumetric image(s) (or a subset thereof—i.e., a 2D cross sectional of a volumetric image) generated using the registrations of breathing correlated images and the registrations of cardiac correlated images, or any combination of the foregoing.

It should be noted that as used in this specification, the term "breathing correlated images" refer to two or more images that correspond with different respective breathing bins, with each image having image data that are generated for the same breathing bin, wherein the images may be two-dimensional (2D) images or three-dimensional (3D) images. Similarly, the term "cardiac correlated images" refers to two or more images that correspond with different respective cardiac bins, with each image having image data that are generated for the same cardiac bin, wherein the images may be 2D images or 3D images.

In some embodiments, the number of projection images from the corresponding combined bin (e.g., combined phase bin, combined amplitude bin, etc.) used by the processor to construct the additional volumetric image may be more than the number of projection images from that bin to construct the initial volumetric image. In other embodiments, the number of projection images from the corresponding bin used by the processor to construct the additional volumetric image may be equal to the number of projection images from that bin combination used to construct the initial volumetric image. In further embodiments, the number of projection images from the corresponding bin combination used by the processor to construct the additional volumetric image may be less than the number of projection images from that bin combination used to construct the initial volumetric image.

Also, in other embodiments, instead of using all of the available projection images from all of the combined bins (e.g., combined phase bins, combined amplitude bins, etc.), a subset of all of the available projection image may be used to construct a new volumetric image. For example, in other embodiments, the new volumetric image may be determined using at least 50%, and more preferably at least 75%, and even more preferably at least 90%, of all of the projection images from all of the sets (e.g., phase bins, amplitude bins, etc.).

In addition, in one or more embodiments, the projection images at the different bin combinations (e.g., phase bins, amplitude bins, etc.) may be all generated during an image session (e.g., in a day). For example, all of the projection images at the different bins may be generated while the patient 28 is at the patient support 14. In such cases, the projection images at the different bin combinations may be generated in a sequence by rotating the gantry 12 to place the radiation source 20 at different gantry angles. In other embodiments, projection images at the different combined bins (e.g., phase bins, amplitude bins, etc.) may be generated from different image sessions. For example, images generated while the patient's physiological cycle is anywhere from 0°-90° in phase taken on day 1 may be binned together with images for the same phase range (i.e., images generated while the patient's physiological cycle is anywhere from 0°-90°) taken on day 2. In some embodiments, such technique may be employed to reduce the radiation dose for the patient. For example, after obtaining some projection images (from previous imaging sessions that occurred in one or more days), the patient may be deemed as having predictable breathing motion and/or cardiac motion, and it may not be necessary to obtain all of the projection images in any further imaging session(s) (e.g., in the current imaging session). In some embodiments, in the current imaging session, the radiation system 10 may be used to obtain a reduced number of projection images. In some cases, the reduced number of projection images may be used in conjunction with the previously obtained projection images to obtain new registrations R. In other cases, the previously created registrations R may be relied upon and re-used, and the projection images obtained in the current imaging session may be used as verification for the previously created registrations R.

Furthermore, in one or more embodiments, the screen 56 may display one or more information that is involved in the method 200. For example, in some embodiments, the screen 56 may display the original projection image(s) P, the modified projection image(s), the new volumetric image(s), or a combination of the foregoing. Also, in some embodiments, the new volumetric images may be displayed in a sequence to form a video. Furthermore, one or more information that is involved in the method 200 may be stored in a non-transitory medium for later processing and/or for retrieval. For example, in some embodiments, a non-transitory medium may store the original projection image(s) P, the modified projection image(s), the new volumetric image(s), etc. In some embodiments, the volumetric images may be stored in a sequence in a form of a video.

In one or more embodiments, a self-correction technique may be implemented in order to reduce and/or eliminate residual approximation errors associated with applying the various registrations to projection images from other combined phase bins in order to generate more additional volumetric images for a particular combined phase bin. In order to perform a self-correction of the motion estimation process of the respective physiological cycle, a synthetic dataset may be created through a simulated measurement process of various projection images. This synthetic dataset may be preprocessed and reconstructed in order to eliminate any motion artifacts. The resulting volumetric image may be forward projected at the same gantry positions where the original projection images were generated. In some cases, registration(s) R is determined on volumetric image(s) from synthetic dataset, and the registration(s) R is compared to other R in order to determine an intrinsic error. In other embodiments, the resulting volumetric image may be compared against the original volumetric image in order to determine an intrinsic error in the motion estimation process. The determined intrinsic error may then be used in order to perform a self-correction of the various registrations between one combined phase bin to another combined phase bin.

Figure 11A:
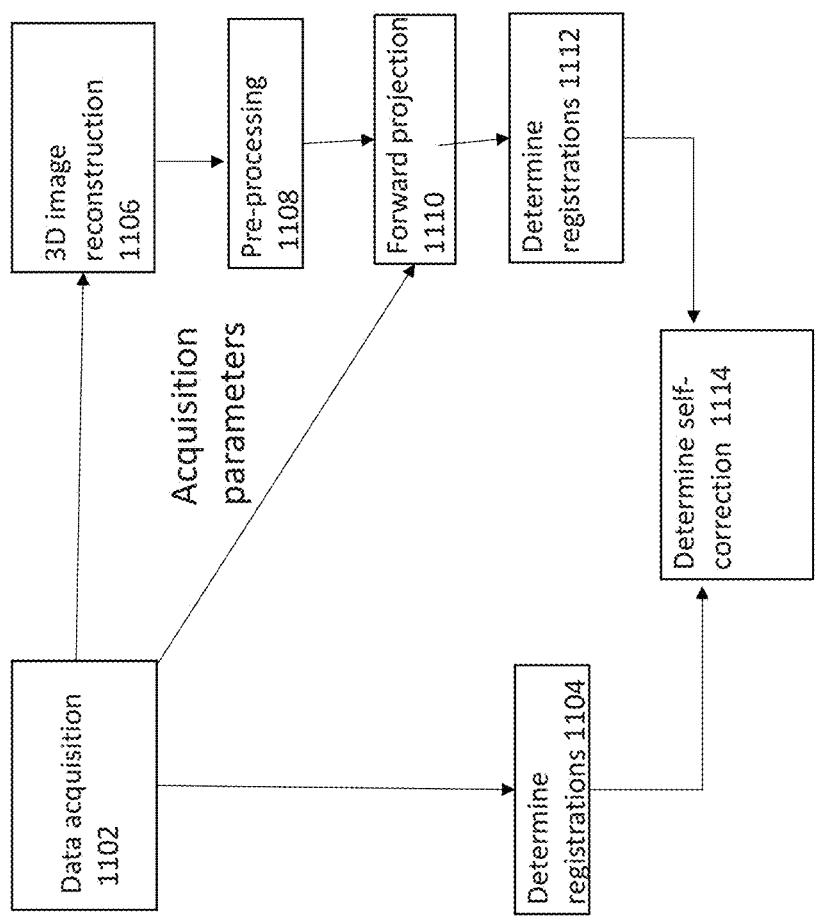
FIGS. 11A and 11B illustrate techniques for determining self-correction in accordance with some embodiments.

In particular, referring now to FIG. 11A, at 1102, projection images are acquired. At 1104, registrations are determined between the various combined phase bins, as explained in detail above. In other words, the left side of FIG. 11A simply describes the process of utilizing initial volumetric images to obtain additional volumetric images for each of the combined phase bins.

At 1106, a simulated data set is created using, the acquired data, and 3D image reconstruction is performed. At 1108, this simulated data is pre-processed to remove unnecessary information. At 1110, this data is forward projected to create simulated additional volumetric images for each of the combined phase bins. It should be noted that acquisition parameters are transferred from the acquired data to the forward projected data. At 1112, the forward projected data for the additional volumetric images for each combined phase bin is used in order to determine registrations between the various volumetric images.

At 1114, the determined registrations at 1112 are compared to the originally determined registrations (step 1104) in order to determine the self-correction. It should be appreciated that the left side of FIG. 11A accounts for both motion and error, whereas the right side of FIG. 11A accounts only for error. Thus, this technique may also be used to determine various parameters related to motion (e.g., cardiac motion or breathing motion).

Figure 11B:
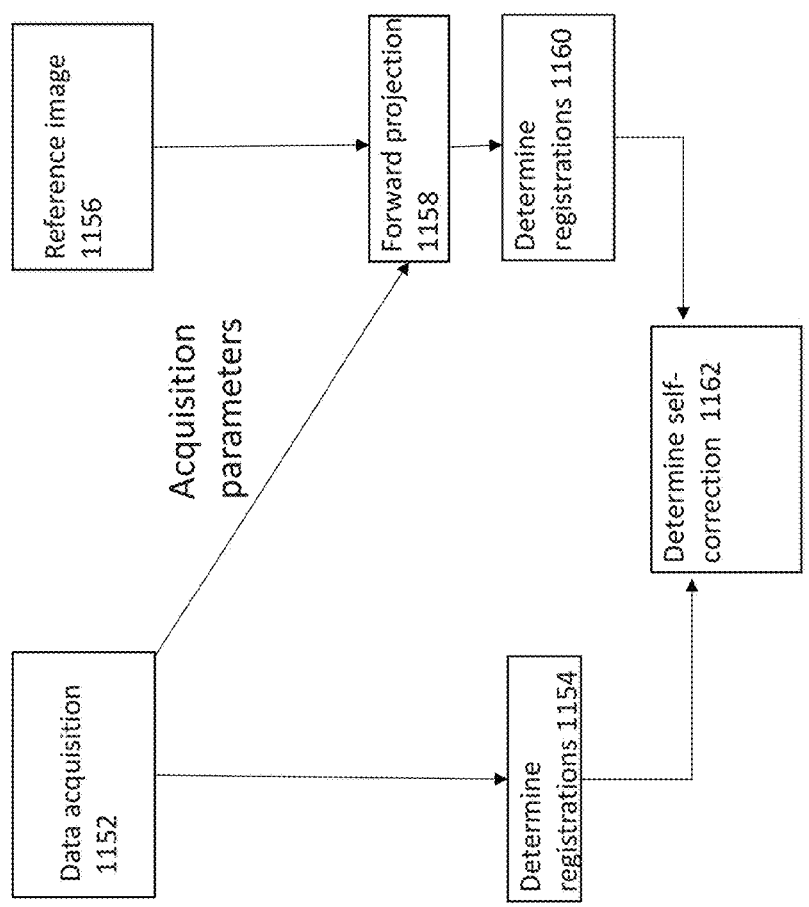

Similarly, FIG. 11B illustrates a similar self-correction technique if a reference CT scan (or any of other type of image, such as CBCT from previous session) is used. At 1152, projection image data is acquired. At 1154, deformable registrations are determined between volumetric images of each of the combined phase bins. At 1156, the reference CT image is determined. At 1158, the reference CT image is forward projected in order to determine additional volumetric images for each of the combined phase bins. At 1160, deformable registrations are determined between the simulated additional volumetric images. At 1162, the registrations determined at 1154 are compared to the registrations determined at 1160 to determine the self-correction. In one or more embodiments, it may simply be a subtraction function. In other embodiments, it may be a more complication function.

Figure 12:
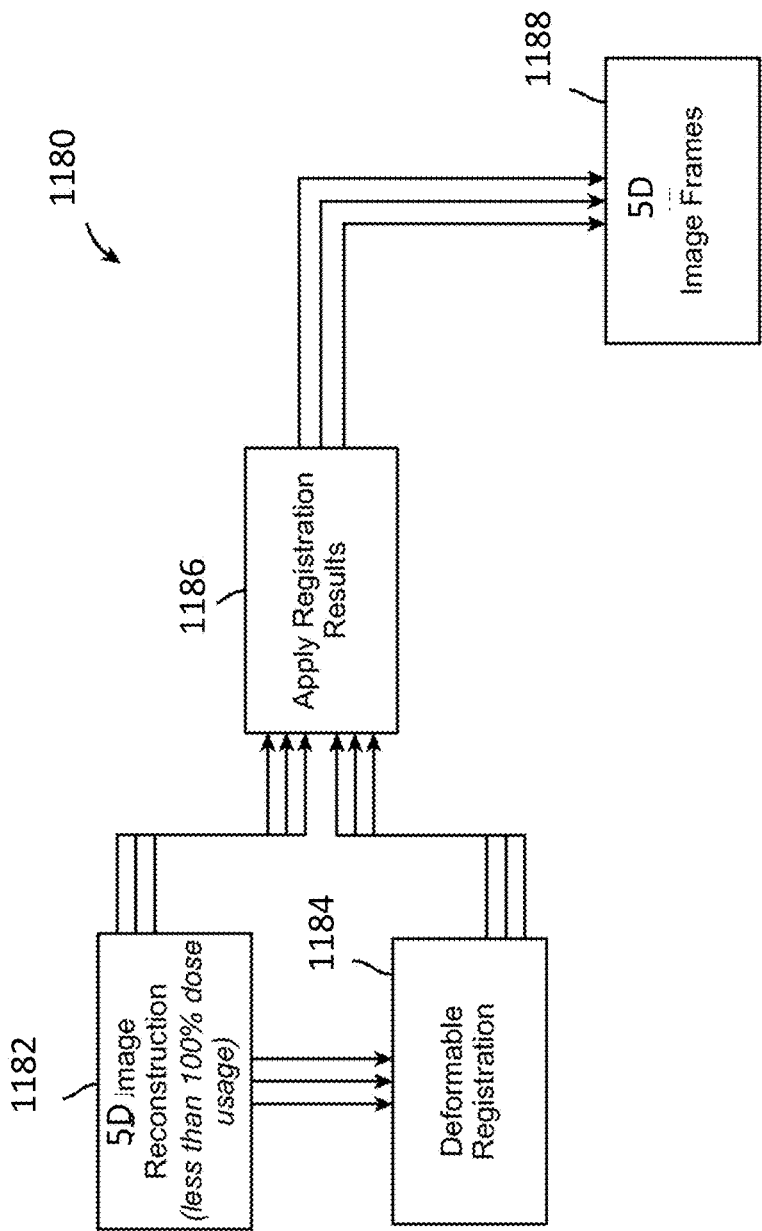
FIG. 12 illustrates a system for obtaining additional volumetric images in accordance with some embodiments.

FIG. 12 illustrates a system 1180 for performing the method 200 in accordance with some embodiments. In one implementation, the system 1180 may be used to carry out the technique described with reference to FIGS. 10A-10D, and/or any of other embodiments described previously. The system 1180 may be implemented using hardware, software, or combination of both. In some embodiments, the system 1180 may be implemented using a processor (e.g., the processor 54), such as a general processor that is specifically configured to perform various functions (e.g., construction of volumetric image(s), deformation registration, modification of projection images, etc.) described herein. In other embodiments, the system 1180 may be implemented using an ASIC. Also, in other embodiments, the system 1180 may be implemented using a processing system. As shown in the figure, the system 1180 includes a module 1182 for obtaining volumetric image(s), a module 1184 for determining registration between volumetric images, a module 1186 for applying the determined registration to projection images, and a module 1188 for determining new (additional) volumetric image(s). In some embodiments, the module 1182 is configured (e.g., built and/or programmed) to perform the functions described with reference to Item 202 of method 200. For example, the module 1182 may be configured to obtain the initial volumetric image(s) by receiving the volumetric image(s). In other embodiments, the module 1182 may be configured to obtain the initial volumetric image(s) by performing image reconstruction using projection images. In some embodiments, the module 1182 may be configured to use a subset (i.e., not all) of the projection images in each set (e.g., phase bins, amplitude bin, etc.) to construct a volumetric image. In other embodiments, the module 1182 may be configured to use all of the projection images in each set to construct a volumetric image.

The module 1184 is configured (e.g., built and/or programmed) to determine registration between volumetric images, such as between two volumetric images corresponding to different combined phase bins like that described with reference to FIG. 6 or FIG. 10C, or between an initial volumetric image and a reference image 800 like that described with reference to FIG. 8B. Thus, any of the functions regarding image registration (e.g., deformable registration) described with reference to the embodiments of FIG. 6 or 8B or 10C may be performed by the module 1184. In other embodiments, the module 1184 may be configured to work on a different dataset, such as planning CT. In addition, in other embodiments, instead of performing registration between volumetric images (3D-3D registration), the module 1184 may be configured to perform registration between two-dimensional images (2D-2D registration), such as between projection images. In further embodiments, the module 1184 may be configured to perform registration between a two dimensional image and a three dimensional image (2D-3D registration). Also, in further embodiments, the module 1184 may be configured to replace each combination of registrations by the resulting deformation registration of the respective volumetric images. For example, the combined registration of R1, R9 may be replaced by the deformation registration between volumetric images that are not adjacent to each other, or that do not have at least one phase bin in common with each other.

The module 1186 is configured (e.g., built and/or programmed) to apply the determined registration(s) R for modifying the projection images P, like that described with reference to the method 200. For example, in some embodiments, the module 1186 may be configured to apply different registration(s) to the projection images in different sets, like that described with reference to the embodiments of FIG. 6 or 8 or 10C, to thereby determine one or more modified projection images.

The module 1188 is configured (e.g., built and/or programmed) to use the modified projection images to construct a new (additional) volumetric image, like that described with reference to Item 204 of the method 200, and the technique of FIG. 6 or 8 or 10C. For example, in some embodiments, the module 1188 may be configured to construct an additional volumetric image for a particular combined bin (e.g., phase bin, amplitude bin, etc.) using projection images from that bin, as well as projection images from other bins. In some embodiments, the number of projection images from the corresponding bin used by the module 1188 to construct the additional volumetric image may be more than the number of projection images from that bin used by the module 1182 to construct the initial volumetric image. In other embodiments, the number of projection images from the corresponding bin used by the module 1188 to construct the additional volumetric image may be equal to the number of projection images from that bin used by the module 1182 to construct the initial volumetric image. Also, in other embodiments, the items 1186, 1188 may be combined, in which cases, the registration(s) R may be directly incorporated in the construction of a new (additional) volumetric volume without performing the intermediate act of modifying the projection images P. In addition, in some embodiments, the registration(s) R, or some analysis results of R may be the final output. In such cases, there is no need to determine any additional volumetric image. In further embodiments, only one volumetric image is required instead of a series of volumetric images.

In the above embodiments, the deformation registration has been described as being performed in an image space to estimate motion (motion vector fields). In other embodiments, the registration (e.g., deformation registration) may be performed in the projection image space (e.g., 2D-2D registration). In such cases, the module 1182 is not required, and the module 1184 is configured to perform deformation registration(s) between projection images in the different respective bins (e.g., phase bins, amplitude bins, etc.). The registration(s) may then be used to determine a new volumetric image. In further embodiments, the registration may be a 2D-3D registration (i.e., registration between a two dimensional image and a volumetric image).

In some cases, 5D CT/CBCT images may have noise that is associated with an amount of dose delivered to the patient being imaged. For example, one objective of an imaging procedure for 5D CT/CBCT may be to use as little dose as possible. However, using less dose generally results in higher noise, and lower image quality. Although the noise may be reduced by increasing dose to patient, such technique may result in undesirable additional dose to the patient. Embodiments described herein may allow noise in 5D CT/CBCT images to be reduced without increasing dose to the patient compared to a 3D image. This is because by "borrowing" projection images from different combined sets (e.g., phase bins, amplitude bins, etc.), i.e., projection images generated when the patient is at different movement states, to construct the volumetric image for a certain movement state, the resulting volumetric image may have less noise without increasing dose to the patient.

In some embodiments, image(s) from different phase(s) of a motion cycle (respiratory, cardiac, or other) may be used to reduce noise for an image at a certain bin (e.g., phase bin, amplitude bin, etc.). In one implementation, the processor (e.g., processor 54) may be configured to deform an image (e.g., a reconstructed 3D image, or a slice of such 3D image) from another bin (source image) to look like the subject image. For example, the processor may perform a deformation registration between the source image and the subject image. Then the processor may perform a local-regional analysis to determine a similarity between the source image and the subject image. The processor then uses the determined similarity to determine a mixing weight, which is then applied by the processor to form a blended composite image using information from the source image and the subject image. Such technique is particularly beneficial if image at different bin does not change significantly, or if image at different bin may be accurately deformed to look like that in the subject image. In some cases, the deformed image may be significantly different from the subject image. In such cases, this technique may set the blending weight of the deformed image to 0. In some embodiments, the determination of the composite image may be performed by the processor using projection image data (i.e., before reconstruction of the volumetric image). In other embodiments, the processor may be configured to use the volumetric images to determine of the composite image. In some embodiments, the processor may use an image from an adjacent bin (e.g., phase bin, amplitude bin, etc.) in the above technique. In other embodiments, instead of the image at the adjacent bin, the processor may use other image(s) at other bin(s) that is not immediately adjacent to the image at the current bin. Also, in some embodiments, the processor may apply different weight factors when using images from different bins.

The above described technique may allow the subject image with relatively less noise to be obtained without increasing the dose to the patient. In some embodiments, the same technique may be applied for other subject images (i.e., images for different phases or phase ranges) to obtain a set of 5D CT/CBCT images that are improved versions of the original subject images. In some cases, the resulting 5D CT/CBCT data set with reduced noise may be compressed for storage.

In other embodiments, adjacent image slice(s) may be used to reduce noise for a particular image slice in a volumetric image. In one implementation, adjacent slice image is deformed to look like the subject image. Then local-regional analysis may be performed to determine similarity between the adjacent slice and the subject image. The determined similarity is then used to determine a mixing weight, which is then applied to form a blended composite image using the adjacent image slice and the subject image. Such technique is particularly beneficial if image at adjacent slice does not change significantly, or if image at adjacent slice may be accurately deformed to look like that in the subject image. In some cases, the deformed adjacent slice may be significantly different from the subject image. In such cases, this technique may set the blending weight of the adjacent image slice to 0. In other embodiments, instead of adjacent image slice(s), the processor may be configured to use other image slice(s) that is not immediately next to the current slice. Also, in other embodiments, the processor may apply different weight factors when using different slice(s). For example, relatively less weight may be applied for slice that is further away in phase.

One technique to perform the local-regional analysis is to prescribe a multi-dimensional physical distance-to-agreement criteria, and an image value difference criteria. Such may be achieved by entering the criteria into a processor (e.g., through a user interface). For each point in the deformed image, the corresponding point in the subject image is identified by the processor. Then the processor computes the distance between that point and the nearest point in the image falling within the acceptable image value range. If the difference in position is within the distance-to-agreement criteria, and the difference in grey scale is within the tolerance, then the two points are considered "similar," and the two points are used to form a composite point. In some embodiments, the distance to agreement and image value criteria may be used by the processor to determine the mixing weight between the images. For example, the processor may be configured to average the grey scale of the two points. Alternatively, the processor may be configured to combine the grey scale of the two points with respective weight factors.

In other embodiments, the processor (e.g., the processor 54) may be configured to use different functions, e.g., continuous function, linear, exponential, etc., for local-regional analysis. For example, pixel in an image that is closer to the position of the pixel in the subject image may be given more weight by the processor in accordance with the function. Pixels in the image that are further away may have less weight (e.g., which decreases exponentially).

In other embodiments, local-regional analysis may be based on color instead of grey scale. For example, if the color of source pixel is within a certain prescribed tolerance from that of the subject pixel, then the processor may combine the two pixels.

In further embodiments, the local-regional analysis may be performed by the processor based on statistical data. For example, the distance-to-agreement and tolerance parameters may be statistical distributions that are considered by the processor when performing the local-regional analysis.

Figure 13:
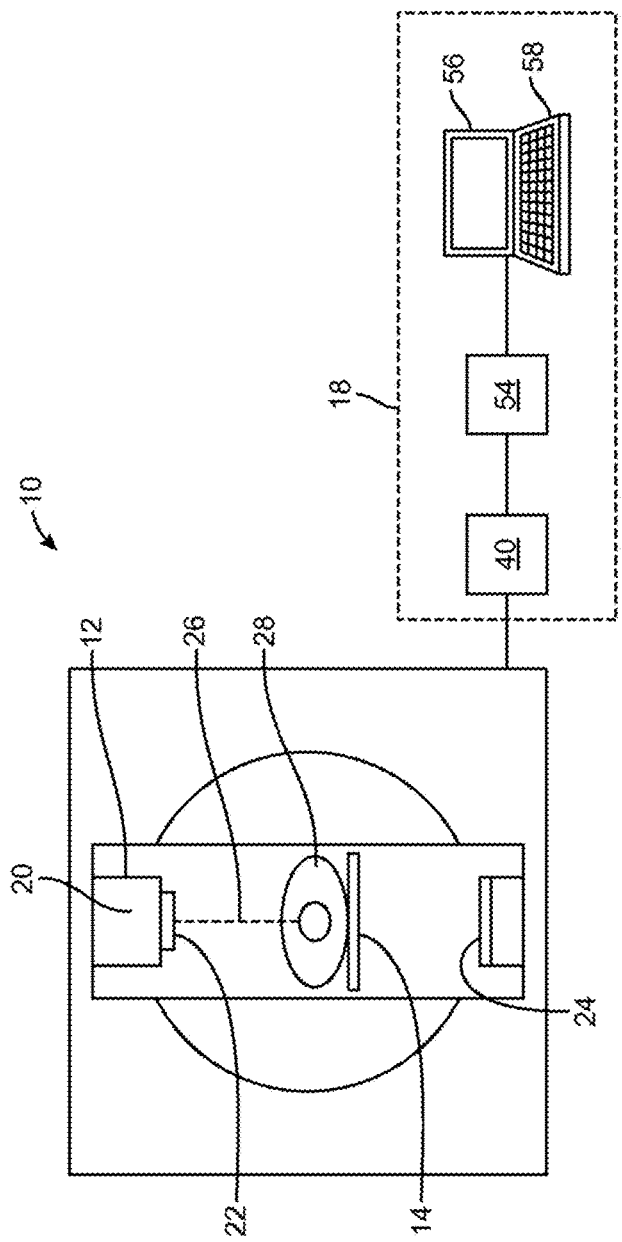
FIG. 13 illustrates another radiation system in accordance with other embodiments.

It should be noted that the system 10 that may be used in the method 200 is not limited to the example described previously. For example, in other embodiments, other imaging systems having different configurations may be used. For example, FIG. 13 illustrates another embodiment of the system 10 that may be used. The system 10 of FIG. 13 is a radiation system that includes a gantry 12, a patient support 14 for supporting a patient, and a control system 18 for controlling an operation of the gantry 12. The gantry 12 is in a form of an arm (e.g., a C-arm). The system 10 also includes a radiation source 20 that projects a beam 26 of radiation towards a patient 28 while the patient 28 is supported on support 14, and optionally a collimator system 22 for controlling a delivery of the radiation beam 26. The radiation source 20 can be configured to generate a cone beam, a fan beam, or other types of radiation beams in different embodiments. In the illustrated embodiments, the radiation source 20 is a diagnostic radiation source for providing diagnostic energy. In other embodiments, in addition to, or instead of, being a diagnostic radiation source, the radiation source 20 may be a treatment radiation source for providing treatment energy.

It should be noted that as used in this specification, the term "processor" (such as the processor 54) may refer to one or more processing units, such as one or more processors, which may or may not be a part of the system 10. Also, one or more functions described with reference to the processor 54 may be performed at least in part by the processor 54, completely by the processor 54, or completely by another processor (which may or may not be a part of the system 10). Also, the term "processor" may include one or more processing units, and may refer to any device that is capable of performing mathematical computation implemented using hardware and/or software.

In addition, it should be noted that the terms "first" and "second" (e.g., as in "first image" and "second image", "first phase", "second phase", etc.) refer to two things/items that are different or separate, and therefore, do not necessarily refer to the order in which the things are generated or arranged.

Also, the term "image" needs not be limited to an image that is displayed visually, and may refer to image data that is stored.

In addition, as used in this specification, the term "phase" may refer to a single phase or a range of phases. Similarly, the term "amplitude" may refer to a single amplitude or a range of amplitudes.

Furthermore, when a volumetric image is described as being determined "using" certain information (e.g., projection image(s), modified projection image(s), data (e.g., data regarding a registration, such as a matrix, a matrix value, a deformed volumetric image, a forward projection of a deformed image, etc.), etc.), it may refer to the information being used directly, or indirectly, to determine the volumetric image. Also, the information stated is not necessarily the only item that is "used" to determine the volumetric image. For example, with reference to the examples described in which projection images P are modified, and the modified projection images P' are then used to determine a volumetric image 600, it may be described that the volumetric image 600 is determined "using" a projection image P (because one of the projection images P is used in a process (in which the projection image P is modified) to determine the volumetric image 600).

Processing System Architecture

Figure 14:
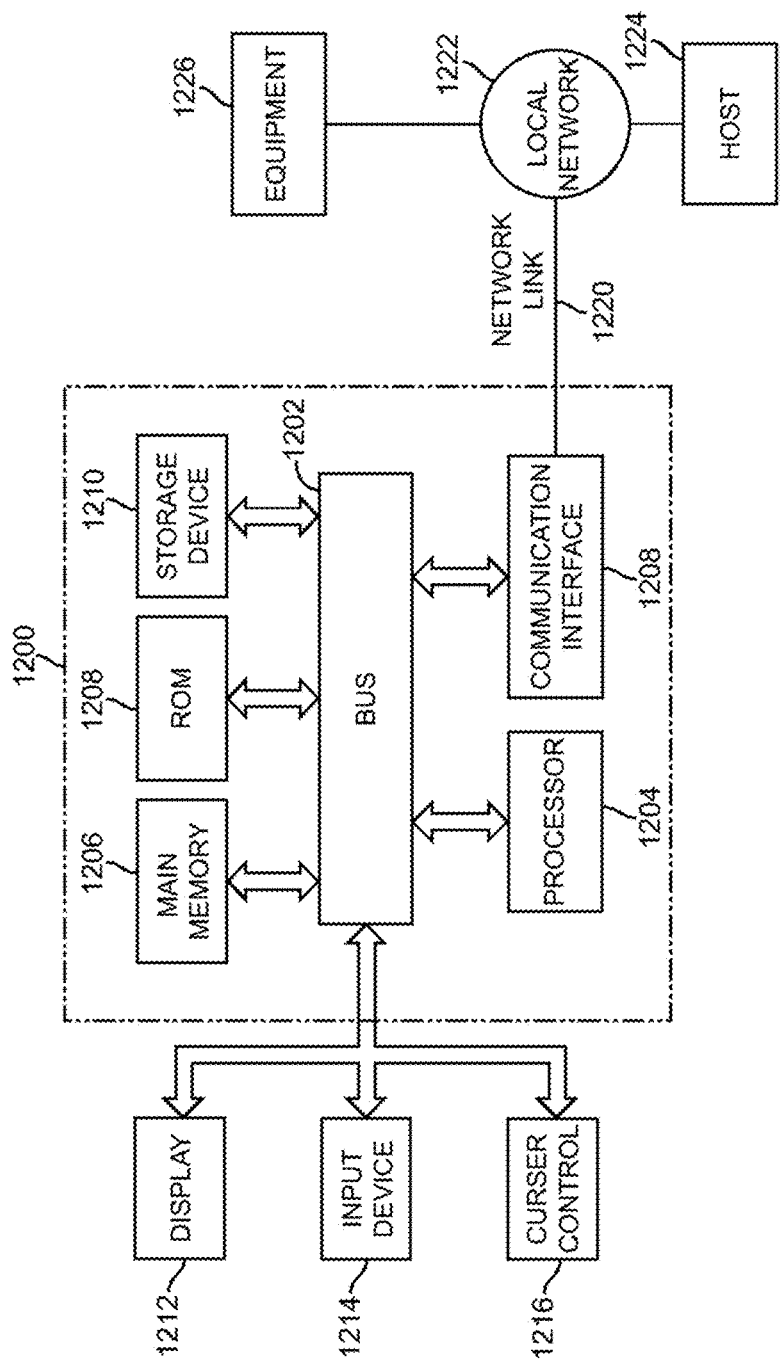
FIG. 14 is a block diagram of a computer system architecture, with which embodiments described herein may be implemented.

FIG. 14 is a block diagram that illustrates an embodiment of a processing system 1200 upon which embodiments described herein may be implemented. Processing system 1200 includes a bus 1202 or other communication mechanism for communicating information, and a processor 1204 coupled with the bus 1202 for processing information. The processor 1204 may be an example of the processor 54 of FIG. 1, or another processor that is used to perform various functions described herein. In some cases, the processing system 1200 may be used to implement the processor 54.

In some cases, the processing system 1200 (e.g., the processor 1204 therein) may include (1) a first volumetric image generator to perform item 1002 (e.g., to reconstruct volumetric images using projection images from their respective breathing phase bins), (2) a first registration engine configured to perform item 1004 (e.g., to determine registrations of images with respect to breathing (breathing correlated images), wherein the registrations may be 2D-2D registrations, 3D-3D registrations, or 2D-3D registrations), (3) a second volumetric image generator to perform item 1006 (e.g., to construct volumetric images for the different combinations of breathing-cardiac phases), (4) a third volumetric image generator for performing item 1010 (e.g., to construct cardiac correlated images, which may be 2D or 3D images), (5) a second registration engine configured to perform item 1012 (e.g., to determine registrations of cardiac correlated images, wherein the registrations may be 2D-2D registrations, 3D-3D registrations, or 2D-3D registrations), and (6) a fourth volumetric image generator for performing item 1016 (e.g., to determine additional or improved volumetric image(s) using the registrations of breathing correlated images and the registrations of cardiac correlated images, or any combination of two or more of the foregoing.

Also, in some cases, the processing system 1200 may be a specialized processing system with features and/or functions that are unique and novel.

The processing system 1200 also includes a main memory 1206, such as a random access memory (RAM) or other dynamic storage device, coupled to the bus 1202 for storing information and instructions to be executed by the processor 1204. The main memory 1206 also may be used for storing temporary variables or other intermediate information during execution of instructions to be executed by the processor 1204. The processing system 1200 further includes a read only memory (ROM) 1208 or other static storage device coupled to the bus 1202 for storing static information and instructions for the processor 1204. A data storage device 1210, such as a magnetic disk or optical disk, is provided and coupled to the bus 1202 for storing information and instructions.

The processing system 1200 may be coupled via the bus 1202 to a display 1212, such as a cathode ray tube (CRT), for displaying information to a user. An input device 1214, including alphanumeric and other keys, is coupled to the bus 1202 for communicating information and command selections to processor 1204. Another type of user input device is cursor control 1216, such as a mouse, a trackball, or cursor direction keys for communicating direction information and command selections to processor 1204 and for controlling cursor movement on display 1212. This input device typically has two degrees of freedom in two axes, a first axis (e.g., x) and a second axis (e.g., y), that allows the device to specify positions in a plane.

The processing system 1200 may be used for performing various functions (e.g., calculation) in accordance with the embodiments described herein. According to one embodiment, such use is provided by processing system 1200 in response to processor 1204 executing one or more sequences of one or more instructions contained in the main memory 1206. Such instructions may be read into the main memory 1206 from another processor-readable medium, such as storage device 1210. Execution of the sequences of instructions contained in the main memory 1206 causes the processor 1204 to perform the process steps described herein. One or more processors in a multi-processing arrangement may also be employed to execute the sequences of instructions contained in the main memory 1206. In alternative embodiments, hard-wired circuitry may be used in place of or in combination with software instructions to implement features of the embodiments described herein. Thus, embodiments described herein are not limited to any specific combination of hardware circuitry and software.

The term "processor-readable medium" as used herein refers to any medium that participates in providing instructions to the processor 1204 for execution. Such a medium may take many forms, including but not limited to, non-volatile media, volatile media, and transmission media. Non-volatile media includes, for example, optical or magnetic disks, such as the storage device 1210. A non-volatile medium may be considered to be an example of a non-transitory medium. Volatile media includes dynamic memory, such as the main memory 1206. A volatile medium may be considered to be another example of a non-transitory medium. Transmission media includes coaxial cables, copper wire and fiber optics, including the wires that comprise the bus 1202. Transmission media can also take the form of acoustic or light waves, such as those generated during radio wave and infrared data communications.

Common forms of processor-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a processor can read.

Various forms of processor-readable media may be involved in carrying one or more sequences of one or more instructions to the processor 1204 for execution. For example, the instructions may initially be carried on a magnetic disk of a remote computer. The remote computer can load the instructions into its dynamic memory and send the instructions over a telephone line using a modem. A modem local to the processing system 1200 can receive the data on the telephone line and use an infrared transmitter to convert the data to an infrared signal. An infrared detector coupled to the bus 1202 can receive the data carried in the infrared signal and place the data on the bus 1202. The bus 1202 carries the data to the main memory 1206, from which the processor 1204 retrieves and executes the instructions. The instructions received by the main memory 1206 may optionally be stored on the storage device 1210 either before or after execution by the processor 1204.

The processing system 1200 also includes a communication interface 1218 coupled to the bus 1202. The communication interface 1218 provides a two-way data communication coupling to a network link 1220 that is connected to a local network 1222. For example, the communication interface 1218 may be an integrated services digital network (ISDN) card or a modem to provide a data communication connection to a corresponding type of telephone line. As another example, the communication interface 1218 may be a local area network (LAN) card to provide a data communication connection to a compatible LAN. Wireless links may also be implemented. In any such implementation, the communication interface 1218 sends and receives electrical, electromagnetic or optical signals that carry data streams representing various types of information.

The network link 1220 typically provides data communication through one or more networks to other devices. For example, the network link 1220 may provide a connection through local network 1222 to a host computer 1224 or to equipment 1226 such as a radiation beam source or a switch operatively coupled to a radiation beam source. The data streams transported over the network link 1220 can comprise electrical, electromagnetic or optical signals. The signals through the various networks and the signals on the network link 1220 and through the communication interface 1218, which carry data to and from the processing system 1200, are exemplary forms of carrier waves transporting the information. The processing system 1200 can send messages and receive data, including program code, through the network(s), the network link 1220, and the communication interface 1218.

It should be noted that the terms "first", "second", "third", etc., are used to distinguish different items, and do not necessarily convey order. For example, "first volumetric image generator" and "second volumetric image generator" are used to identify two image generators. Thus, the designation of "volumetric image generator" may be used interchangeably—e.g., first volumetric image generator may be referred to as a second volumetric image generator, or a third volumetric image generator, etc.

In addition, the term "registration" may refer to one or more registration(s).

Also, as used in this specification, the term "image" does not necessarily refer to image that is visually displayed, and may refer to image data that is stored or being processed.

Although particular embodiments have been shown and described, it will be understood that it is not intended to limit the claimed inventions, and it will be obvious to those skilled in the art that various changes and modifications may be made. The specification and drawings are, accordingly, to be regarded in an illustrative rather than restrictive sense. The claimed inventions are intended to cover alternatives, modifications, and equivalents.

What is claimed:

1. An apparatus, comprising:
an input configured to receive a plurality of images, wherein the images include respective sub-images of a bodily part of a subject, and wherein a position of the bodily part relates to a breathing movement and a cardiac movement of the subject;
a first registration engine configured to determine a first registration of at least two breathing correlated images, wherein the at least two breathing correlated images comprise two of the plurality of images or are derived from at least some of the plurality of images;
a second registration engine configured to determine a second registration of at least two cardiac correlated images; and
a volumetric image generator configured to generate a volumetric image using the first registration and the second registration.

2. The apparatus of claim 1, wherein the first registration comprises a 2D-to-2D image registration.

3. The apparatus of claim 1, wherein the first registration comprises a 3D-to-3D image registration.

4. The apparatus of claim 1, wherein the first registration comprises a 2D-to-3D image registration.

5. The apparatus of claim 1, wherein the at least two breathing correlated images are generated during an imaging session.

6. The apparatus of claim 1, wherein the at least two breathing correlated images correspond with different respective breathing bins, and wherein each of the at least two breathing correlated images comprises image data that are for a same one of the breathing bins.

7. The apparatus of claim 1, wherein the at least two cardiac correlated images correspond with different respective cardiac bins, and wherein each of the at least two cardiac correlated images comprises image data that are for a same one of the cardiac bins.

8. The apparatus of claim 1, further comprising a cardiac correlated image generator configured to generate the at least two cardiac correlated images.

9. The apparatus of claim 8, wherein the cardiac correlated image generator is configured to generate the at least two cardiac correlated images based on the first registration.

10. The apparatus of claim 8, further comprising a non-transitory medium storing the plurality of images in association with a number N1 of breathing stages and in association with a number N2 of cardiac stages.

11. The apparatus of claim 10, further comprising a breathing-cardiac image generator configured to generate N1×N2 number of breathing-cardiac images for the different combinations of breathing-cardiac stages.

12. The apparatus of claim 11, wherein the cardiac correlated image generator is configured to generate the at least two cardiac correlated images based on the first registration and based on a subset of the N1×N2 number of breathing-cardiac images.

13. The apparatus of claim 1, wherein the volumetric image generator is configured to generate the volumetric image also using at least 50% of the plurality of images, wherein the plurality of images is generated while the subject is undergoing different breathing stages and cardiac stages.

14. The apparatus of claim 1, wherein the volumetric image generator is configured to generate the volumetric image also using at all of the plurality of images, wherein the plurality of images is generated while the subject is undergoing different breathing stages and cardiac stages.

15. An image processing method, comprising:
obtaining a plurality of images, wherein the images include respective sub-images of a bodily part of a subject, and wherein a position of the bodily part relates to a breathing movement and a cardiac movement of the subject;
determining, using a first registration engine, a first registration of at least two breathing correlated images, wherein the at least two breathing correlated images comprise two of the plurality of images or are derived from at least some of the plurality of images;
determining, using a second registration engine, a second registration of at least two cardiac correlated images; and
generating, using a volumetric image generator, a volumetric image using the first registration and the second registration.

16. The method of claim 15, wherein the first registration comprises a 2D-to-2D image registration.

17. The method of claim 15, wherein the first registration comprises a 3D-to-3D image registration.

18. The method of claim 15, wherein the first registration comprises a 2D-to-3D image registration.

19. The method of claim 15, wherein the at least two breathing correlated images are generated during an imaging session.

20. The method of claim 15, wherein the at least two breathing correlated images correspond with different respective breathing bins, and wherein each of the at least two breathing correlated images comprises image data that are for a same one of the breathing bins.

21. The method of claim 15, wherein the at least two cardiac correlated images correspond with different respective cardiac bins, and wherein each of the at least two cardiac correlated images comprises image data that are for a same one of the cardiac bins.

22. The method of claim 15, further comprising generating, using a cardiac correlated image generator, the at least two cardiac correlated images.

23. The method of claim 22, wherein the at least two cardiac correlated images are generated based on the first registration.

24. The method of claim 22, further comprising storing the plurality of images in association with a number N1 of breathing stages and in association with a number N2 of cardiac stages.

25. The method of claim 24, further comprising generating, using a breathing-cardiac image generator, N1×N2 number of breathing-cardiac images for the different combinations of breathing-cardiac stages.

26. The method of claim 25, wherein the at least two cardiac correlated images are generated based on the first registration and based on a subset of the N1×N2 number of breathing-cardiac images.

27. The method of claim 15, wherein the volumetric image is generated also using at least 50% of the plurality of images, wherein the plurality of images is generated while the subject is undergoing different breathing stages and cardiac stages.

28. The method of claim 15, wherein the volumetric image is generated also using at all of the plurality of images, wherein the plurality of images is generated while the subject is undergoing different breathing stages and cardiac stages.

29. A computer product having a non-transitory computer-readable medium storing a set of instruction, an execution of which, by a computer, causes a process to be performed, the process comprising:

obtaining a plurality of images, wherein the images include respective sub-images of a bodily part of a subject, and wherein a position of the bodily part relates to a breathing movement and a cardiac movement of the subject;

determining, using a first registration engine, a first registration of at least two breathing correlated images, wherein the at least two breathing correlated images comprise two of the plurality of images or are derived from at least some of the plurality of images;

determining, using a second registration engine, a second registration of at least two cardiac correlated images; and generating, using a volumetric image generator, a volumetric image using the first registration and the second registration.

* * * * *